United States Patent [19]

Loewe et al.

[11] 4,176,192

[45] Nov. 27, 1979

[54] SUBSTITUTED PHENYLGUANIDINES AND PROCESS FOR THEIR MANUFACTURE

[75] Inventors: Heinz Loewe, Kelkheim; Josef Urbanietz, Schwalbach; Dieter Duwel, Hofheim; Reinhard Kirsch, Niederjosbach, all of Fed. Rep. of Germany

[73] Assignee: Hoechst Aktiengesellschaft, Frankfurt am Main, Fed. Rep. of Germany

[21] Appl. No.: 772,234

[22] Filed: Feb. 25, 1977

[30] Foreign Application Priority Data

Feb. 28, 1976 [DE] Fed. Rep. of Germany ....... 2608238

[51] Int. Cl.² ..................... A61K 31/27; C07C 143/68

[52] U.S. Cl. .................. 424/300; 260/397.6; 260/456 A

[58] Field of Search .......... 260/456 A, 397.6; 424/303, 300

[56] References Cited

U.S. PATENT DOCUMENTS

| 3,996,368 | 12/1976 | Loewe et al. | 260/456 A |
| 3,996,369 | 12/1976 | Loewe et al. | 260/456 A |
| 4,005,123 | 1/1977 | Kolling et al. | 424/303 |

*Primary Examiner*—Nicky Chan
*Attorney, Agent, or Firm*—Curtis, Morris & Safford

[57] ABSTRACT

Substituted phenylguanidines are disclosed as well as a process for their manufacture. The said compounds are active against helminths and liver flukes.

9 Claims, No Drawings

SUBSTITUTED PHENYLGUANIDINES AND PROCESS FOR THEIR MANUFACTURE

The present invention relates to novel substituted phenylguanidines, a process for their manufacture and their use as pharmaceutical compositions, especially as anthelmintics.

Phenylguanidines showing an anthelmintic action have been known from German Offenlegungsschriften Nos. 2 117 293, 2 304 764 and 2 423 679.

Novel substituted phenylguanidines have been found which correspond to the general formula I

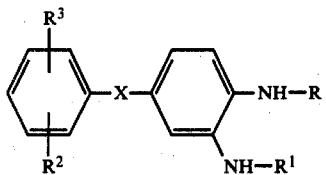

in which R is different from $R^1$ and each represents alternatively one of the radicals

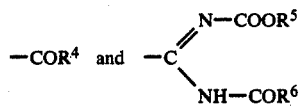

in which $R^4$ is hydrogen, optionally substituted alkyl, optionally substituted cycloalkyl, optionally substituted aryl, optionally substituted amino, optionally substituted alkoxy, or optionally substituted aralkyl, $R^5$ is an optionally substituted alkyl, optionally substituted alkenyl or optionally substituted alkinyl, $R^6$ is hydrogen, optionally substituted alkyl, optionally substituted cycloalkyl, optionally substituted alkoxy, optionally substituted alkenyloxy, optionally substituted alkinyloxy, optionally substituted aryl, optionally substituted aralkyl, optionally substituted alkenyl or optionally substituted alkinyl, and in which $R^2$ and $R^3$, independent of each other, stand for hydrogen, alkoxy having 1 to 4 carbon atoms, halogen, trifluoromethyl, alkyl having 1 to 4 carbon atoms or CN, and X represents the group —O—SO$_2$— or —SO$_2$—O—.

A process has been found to prepare the substituted phenylguanidines of the general formula I, which comprises reacting substituted aniline derivatives of the general formula II

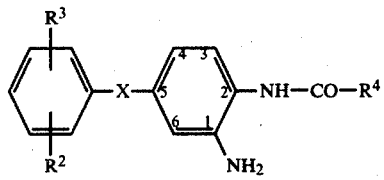

in which $R^2$, $R^3$, $R^4$ and X are defined as in formula I above and X is linked with position 4 or position 5 of the substituted 1-amino-phenyl group of the formula (II), with isothioureas of the general formula III

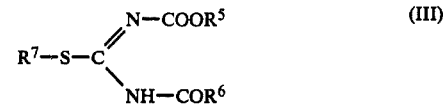

in which $R^5$ and $R^6$ are defined as in formula I and $R^7$ stands for alkyl having 1 to 4 carbon atoms, in the presence of a diluent and optionally in the presence of an acid.

In formulae II and III, the optionally substituted alkyl $R^2$, $R^3$, $R^4$, $R^5$ and $R^6$ is a straight-chained or branched alkyl having preferably 1 to 6, especially 1 to 4 carbon atoms. As an example, there may be mentioned optionally substituted methyl, ethyl, n- and i-propyl, n-, i- and t-butyl.

As optionally substituted alkenyl $R^5$ and $R^6$ in formula III there is present straight-chained or branched alkenyl having preferably 2 to 6, especially 2 to 4 carbon atoms. As an example, there may be mentioned optionally substituted ethenyl, propenyl-(1), propenyl-(2) and butenyl-(3).

As optionally substituted alkinyl $R^5$ and $R^6$ in formula III there is present straight-chained or branched alkinyl having preferably 2 to 6, especially 2 to 4 carbon atoms. As an example, there may be mentioned optionally substituted ethinyl, propinyl-(1), propinyl-(2) and butinyl-(3).

As optionally substituted alkoxy $R^2$, $R^3$, $R^4$, $R^6$ in formulae II and III there is present straight-chained or branched alkoxy having 1 to 4 carbon atoms. As an example, there may be mentioned optionally substituted methoxy, ethoxy, n- and i-propoxy and n-, i- and t-butoxy.

As halogen $R^2$, $R^3$ in formula II there is present preferably fluorine, chlorine, bromine and iodine, especially fluorine, chlorine and bromine.

As optionally substituted aryl $R^4$ and $R^6$ in formulae II and III there is present aryl having preferably 6 or preferably 6 to 10 carbon atoms in the aryl moiety. As an example, there may be mentioned optionally substituted phenyl or naphthyl.

As optionally substituted aralkyl $R^4$ and $R^6$ in formula III there is present aralkyl optionally substituted in the aryl moiety and/or alkyl moiety having preferably 6 or 10, especially 6 carbon atoms in the aryl moiety and preferably 1 to 4, especially 1 or 2 carbon atoms in the alkyl moiety, the alkyl moiety optionally being straight-chained or branched. As an example, there may be mentioned optionally substituted benzyl and phenylethyl.

As optionally substituted cycloalkyl $R^4$, $R^6$ in formulae II and III there is present mono-, bi- and tricyclic cycloalkyl having preferably 3 to 10, especially 3, 5 or 6 carbon atoms. As an example, there may be mentioned optionally substituted cyclopropyl, cyclobutyl, cyclopentyl, cyclohexyl, cycloheptyl, bicyclo-[2,2,1]-heptyl, bicyclo-[2,2,2]-octyl and adamantyl.

As optionally substituted alkenyloxy $R^6$ in formula III there is present straight-chained or branched alkenyloxy having preferably 2 to 6, especially 2 to 4 carbon atoms. As an example, there may be mentioned optionally substituted ethenyloxy, propenyl-(1)-oxy, propenyl-(2)-oxy and butenyl-(3)-oxy.

As optionally substituted alkinyloxy $R^6$ in formula III there is present straight-chained or branched alkinyl having preferably 2 to 6, especially 2 to 4 carbon atoms.

As an example, there may be mentioned optionally substituted ethinyloxy, propinyl-(1)-oxy, propinyl-(2)-oxy and butinyl-(3)-oxy.

As alkyl $R^7$ in formula III there is present preferably methyl or ethyl.

Preference is given particularly to compounds of the formula I, in which $R^2$ and $R^3$ stand for hydrogen, methyl, ethyl, n-butyl, methoxy, ethoxy, fluorine, chlorine, bromine, cyano or trifluoromethyl, $R^3$ preferably substituting the 3-position of the phenyl ring, whereas $R^2$ is hydrogen, $R^4$: stands for methyl, ethyl, propyl, n-butyl, i-butyl, n-pentyl, n-hexyl, cyclopentyl, cyclohexyl, phenyl, benzyl, methoxymethyl, methoxy, ethoxy, phenoxymethyl, methylamino, ethylamino, n-butylamino, ω-cyanopentylamino, β-methoxyethylamino, $R^5$: stands for methyl, ethyl, i-propyl, sec.-butyl, propenyl-(2), propinyl, $R^6$: stands for methyl, ethyl, propyl, isopropyl, n-amyl, isoamyl, n-butyl, cyclohexyl, phenyl, benzyl, methoxymethyl, phenoxymethyl, allyl, crotyl, methallyl, methoxy, ethoxy-i-propoxy, sec.-butyloxy, propenyl-(2)-oxy, propinyl-(2)-oxy, 2-methyl-propenyl-(2)-oxy.

In the groups $R^4$, $R^5$ and $R^6$ of the compounds of formula I there may be mentioned the following substituents which are optionally present:

$R^4$: for alkyl, the substituents $(C_1-C_2)$-alkoxy, halogen, cyano, $(C_6-C_8)$-aryloxy, preferably methoxy, chlorine or phenoxy; for cycloalkyl, the substituents methyl and ethyl; for aryl, the substituents $(C_1-C_4)$-alkyl, halogen, $(C_1-C_4)$-alkoxy, preferably methyl, chlorine, methoxy; for amino, 1 or 2 $(C_1-C_4)$-alkyl, preferably dimethyl and diethyl; for alkoxy, the substituents $(C_1-C_2)$-alkyl, halogen; for aralkyl, the substituents $(C_1-C_2)$-alkyl, halogen, $(C_1-C_4)$-alkoxy, preferably methyl, chlorine, methoxy.

$R^5$: for alkyl, the substituents $(C_1-C_2)$-alkoxy, halogen, cyano, preferably methoxy or chlorine; for alkenyl and alkinyl, in either case the substituents ethyl and methyl.

$R^6$: for alkyl, $(C_1-C_2)$-alkoxy, halogen, cyano, $(C_6-C_8)$-aryloxy, preferably methoxy, chlorine, phenoxy; for cycloalkyl, the substituents methyl or ethyl; for alkoxy, the substituents methoxy or chlorine; for alkenyloxy and alkinyloxy, in either case methyl or ethyl; for aryl and aralkyl, in either case the substituents $(C_1-C_4)$-alkyl, halogen, $(C_1-C_4)$-alkoxy, preferably methyl, chlorine, methoxy; for alkenyl and alkinyl, in either case the substituents methyl and ethyl.

The thio-ureas used as starting compounds have been defined by formula III. They are partially known (cf. Olin and Dains, J. Amer. Chem. Soc. 52, 3326 (1930) as well as U.S. Pat. No. 2,993,502) and may also easily be obtained by methods analogous to those of known processes. For their preparation, use is generally made of known N-acylthio-ureas as starting compounds [cf. for example, Berichte der deutschen Chemischen Gesellschaft, 6, 755 (1873); Ann. chim. (5) 11, 313 (1877); J. Amer. Chem. Soc. 62, 3274 (1940)], which are also reacted in known manner with alkylating agents, such as alkyl halides, sulfates and sulfonates, to give the corresponding S-alkyl-N-acyl-iso-thio-ureas [cf., for example, J. org. Chem. 30, 560, (1965); Chem. Pharm. Bull. (Tokyo), 9, 245, (1961)]. These S-alkyl-N-acyl-isothio-ureas may then be reacted with halogeno-formic acid-esters or with pyrocarbonic acid-dialkyl-esters [cf. Ber. dtsch. chem. Ges. 71, 1797 (1938)], to give S-alkyl-N-acyl-N;40 -alkoxycarbonyl-isothio-ureas.

This latter reaction corresponds to the principle of the known substitution of S-alkyl-isothio-ureas with chloroformic acid-alkylesters [cf. J. Amer. chem. Soc. 52, 3326 (1930)].

As examples for the isothio-ureas which may be used according to the invention, the following compounds are mentioned:
  N,N'-bis-methoxycarbonyl-S-methyl-isothio-urea (melting point 99° to 100° C.),
  N,N'-bis-ethoxycarbonyl-S-methyl-isothio-urea (melting point 50° to 51° C.),
  N-ethoxycarbonyl-N'-propionyl-S-methyl-isothio-urea (melting point 92° to 94° C.),
  N-methoxycarbonyl-N'-propionyl-S-methyl-isothio-urea (melting point 97° to 99° C.),
  N-methoxycarbonyl-N'-ethoxyacetyl-S-methyl-isothio-urea (melting point 69° to 70° C.),
  N-methoxycarbonyl-N'-cyclohexylcarbonyl-S-methyl-isothio-urea (m.p. 67° to 68° C.),
  N-methoxycarbonyl-N'-phenylacetyl-S-methyl-isothio-urea (m.p. 55° to 56° C.),
  N-ethoxycarbonyl-N'-benzoyl-S-methyl-isothio-urea (m.p. 79° to 80° C.),
  N-ethoxycarbonyl-N'-methoxycarbonyl-S-methyl-isothio-urea (m.p. 69° C.),
  N-allyloxycarbonyl-N'-methoxycarbonyl-S-methyl-isothio-urea,
  N-propinyloxycarbonyl-N'-methoxycarbonyl-S-methyl-isothio-urea,
  N,N'-bis-allyloxycarbonyl-S-methyl-isothio-urea,
  N,N'-bis-propinyloxycarbonyl-S-methyl-isothio-urea.

The substituted 2-amino-anilides used as starting compounds may be easily prepared in a manner analogous to that of processes known in literature.

Thus, for example, 2-amino-4-phenoxysulfonyl-butyranilide can be obtained by reacting 3-nitro-4-chloro-benzene-sulfonic acid-chloride with phenol to yield 2-nitro-4-phenoxysulfonylchloro-benzene, reacting this product with ammonia to give 2-nitro-4-phenoxy-sulfonyl-aniline, acylating this compound with butyryl-chloride to form 2-nitro-4-phenoxysulfonyl-butyranilide, and by subsequently hydrogenating said product catalytically.

On the other hand, for example, 2-amino-4-phenylsulfonyloxypropionanilide may be prepared by reacting benzene-sulfonic acid-chloride with 2-nitro-4-hydroxyaniline to yield 2-nitro-4-phenyl-sulfonyloxy-aniline, by acylating with propionyl-chloride to give 2-nitro-4-phenyl-sulfonyloxy-propionanilide, and by subsequently hydrogenating the product catalytically.

As examples for the 2-amino-anilides used as starting compounds there may be mentioned:
(a)
  2-Amino-4-phenoxysulfonyl-methoxyacetanilide
  2-amino-4-phenoxysulfonyl-acetanilide
  2-amino-4-phenoxysulfonyl-propionanilide
  2-amino-4-phenoxysulfonyl-butyranilide
  2-amino-4-phenoxysulfonyl-iso-butyranilide
  2-amino-4-phenoxysulfonyl-valeranilide
  2-amino-4-phenoxysulfonyl-iso-valeranilide
  2-amino-4-phenoxysulfonyl-capron-anilide
  2-amino-4-phenoxysulfonyl-iso-capron-anilide
  2-amino-4-phenoxysulfonyl-cyclopentane-carbonanilide
  2-amino-4-phenoxysulfonyl-cyclohexane-carbonanilide
  2-amino-4-phenoxysulfonyl-phenylacetanilide 2-amino-4-phenoxysulfonyl-phenoxyacetanilide
2-amino-4-phenoxysulfonyl-benzanilide;

(b)
  2-amino-4-(4-chloro-phenoxysulfonyl)-acetanilide
  2-amino-4-(3-chloro-phenoxysulfonyl)-acetanilide
  2-amino-4-(2-chloro-phenoxysulfonyl)-acetanilide
  and their homologues corresponding to paragraph (a)

(c)
  2-amino-4-(4-bromo-phenoxysulfonyl)-acetanilide
  2-amino-4-(4-methyl-phenoxysulfonyl)-acetanilide
  2-amino-4-(4-t.butyl-phenoxysulfonyl)-acetanilide
  2-amino-4-(4-methoxy-phenoxysulfonyl)-acetanilide
  2-amino-4-(4-ethoxy-phenoxysulfonyl)-acetanilide
  2-amino-4-(4-propoxy-phenoxysulfonyl)-acetanilide
  2-amino-4-(4-isopropoxy-phenoxysulfonyl)-acetanilide
  2-amino-4-(4-butoxy-phenoxysulfonyl)-acetanilide
  2-amino-4-(4-isobutoxy-phenoxysulfonyl)-acetanilide
  2-amino-4-(4-cyano-phenoxysulfonyl)-acetanilide and their position isomers and homologues corresponding to paragraph (b)

(d)
  2-amino-4-(3-trifluoromethyl-phenoxysulfonyl)-acetanilide
  2-amino-4-(3,5-bis-trifluoromethyl-phenoxysulfonyl)-acetanilide and their homologues corresponding to paragraph (a)

(e)
  2-amino-4-(2-chloro-3-methyl-phenoxysulfonyl)-acetanilide
  2-amino-4-(2-chloro-4-methyl-phenoxysulfonyl)-acetanilide
  2-amino-4-(2-chloro-5-methyl-phenoxysulfonyl)-acetanilide
  2-amino-4-(2-chloro-6-methyl-phenoxysulfonyl)-acetanilide
  2-amino-4-(3-chloro-2-methyl-phenoxysulfonyl)-acetanilide
  2-amino-4-(3-chloro-4-methyl-phenoxysulfonyl)-acetanilide
  2-amino-4-(3-chloro-5-methyl-phenoxysulfonyl)-acetanilide
  2-amino-4-(3-chloro-6-methyl-phenoxysulfonyl)-acetanilide
  2-amino-4-(4-chloro-2-methyl-phenoxysulfonyl)-acetanilide
  2-amino-4-(4-chloro-3-methyl-phenoxysulfonyl)-acetanilide and their homologues corresponding to paragraph (a)

(f)
  2-amino-4-(2,3-dichloro-phenoxysulfonyl)-acetanilide
  2-amino-4-(2,4-dichloro-phenoxysulfonyl)-acetanilide
  2-amino-4-(2,5-dichloro-phenoxysulfonyl)-acetanilide
  2-amino-4-(2,6-dichloro-phenoxysulfonyl)-acetanilide
  2-amino-4-(3,4-dichloro-phenoxysulfonyl)-acetanilide
  2-amino-4-(3,5-dichloro-phenoxysulfonyl)-acetanilide and their homologues corresponding to paragraph (a)

(g)
  2-amino-4-(2,3-dimethyl-phenoxysulfonyl)-acetanilide and its position isomers and homologues corresponding to paragraph (f)

(h)
  2-amino-5-phenoxysulfonyl-acetanilide and its analogues corresponding to paragraphs (a) through (g)

(i)
  2-amino-4-phenylsulfonyloxy-acetanilide and its analogues corresponding to paragraphs (a) through (h)

(k)
  2-amino-5-phenylsulfonyloxy-acetanilide and its analogues corresponding to paragraphs (a) through (h)

(l)
  N-(2-amino-4-phenoxysulfonyl-phenyl)-N'-methyl-urea
  N-(2-amino-4-phenoxysulfonyl-phenyl)-N'-ethyl-urea
  N-(2-amino-4-phenoxysulfonyl-phenyl)-N'-butyl-urea
  N-(2-amino-4-phenoxysulfonyl-phenyl)-N'-ω-cyano-pentyl-urea
  N-(2-amino-4-phenoxysulfonyl-phenyl)-N'-β-methoxyethyl-urea
  N-(2-amino-b 4-phenoxysulfonyl-phenyl)-N'-benzyl-urea
  N-(2-amino-4-phenoxysulfonyl-phenyl)-N'-phenyl-urea (m)
  N-(2-amino-4-(4-chloro-phenoxysulfonyl)-phenyl)-N'-methyl-urea
  and its position isomers corresponding to paragraph (b) as well as its homologues corresponding to paragraph (l)

(n)
  N-(2-amino-4-(4-bromo-phenoxysulfonyl)-phenyl)-N'-methyl-urea
  and its analogues corresponding to paragraph (c) as well as its homologues corresponding to paragraph (l)

(p)
  N-(2-amino-4-(3-trifluoromethyl-phenoxysulfonyl-phenyl)-N'-methyl-urea
  N-(2-amino-4-(3,5-bis-trifluoromethyl-phenoxysulfonylphenyl)-N'-methyl-urea
  and their homologues corresponding to paragraph (l)

(q)
  N-(2-amino-4-(2-chloro-3-methyl-phenoxysulfonyl-phenyl)-N'-methyl-urea
  and its position isomers corresponding to paragraph (e) as well as its homologues corresponding to paragraph (l)

(r)
  N-(2-amino-4-(2,3-dichloro-phenoxysulfonyl-phenyl)-N'-methyl-urea
  and its position isomers corresponding to paragraph (f) as well as its homologues corresponding to paragraph (l)

(s)
  N-(2-amino-4-(2,3-dimethyl-phenoxysulfonyl-phenyl)-N'-methyl-urea
  and its position isomers corresponding to paragraph (g) as well as its homologues corresponding to paragraph (l)

(t)
  N-(2-amino-5-phenoxysulfonyl-phenyl)-N'-methyl-urea and its analogues corresponding to paragraphs (l) through (s)

(u)
  N-(2-amino-4-phenylsulfonyloxy-phenyl)-N'-methyl-urea and its analogues corresponding to paragraphs (l) through (t)

(v)
  N-(2-amino-5-phenylsulfonyloxy-phenyl)-N'-methylurea and its analogues corresponding to paragraphs (l) through (t).

When carrying out the process according to the invention, 1 mole of isothio-urea-ether is suitably used per 1 mole of the substituted 2-amino-anilide. The reaction is preferably carried out in a boiling solvent, with alkyl mercaptan being formed as by-product. Upon cooling of the reaction mixture, the final products are obtained in a crystalline form and may be separated by suction-filtration and purified optionally by re-dissolving and/or re-crystallizing.

In the process of the invention there may be used as solvents all polar organic solvents. They include preferably alcohols, such as methanol, ethanol, iso-propanol as well as their mixtures with water, ketones, such as acetone (also in admixture with water), acetic acid (also in admixture with water), but also ethers, such as dioxan or tetrahydrofuran.

The acids added as catalysts promoting the reaction in the process of the invention may as a rule be selected from the series of the known organic or inorganic acids. However, use is made preferably of the easily accessible and technically important representatives of these classes. As examples, there may be mentioned: Hydrochloric acid, sulfuric acid, nitric acid, formic acid, acetic acid, p-toluene-sulfonic acid.

The reaction temperatures may vary within a fairly large range. The reaction is generally carried out at a temperature between 0° C. and 120° C., preferably between 30° and 100° C. It is generally effected at normal pressure.

The novel substituted phenylguanidines of the general formula I of the invention include, for example, the following compounds:

(a)
  N-(2-Acetamido-5-phenoxysulfonyl-phenyl)-N',N''-bis-methoxycarbonylguanidine
  N-(2-acetamido-5-phenoxysulfonyl-phenyl)-N',N''-bis-ethoxycarbonylguanidine
  N-(2-acetamido-5-phenoxysulfonyl-phenyl)-N',N''-bis-propoxycarbonylguanidine
  N-(2-acetamido-5-phenoxysulfonyl-phenyl)-N',N''-bis-isopropoxycarbonyl-guanidine
  N-(2-acetamido-5-phenoxysulfonyl-phenyl)-N',N''-bis-butoxycarbonylguanidine
  N-(2-acetamido-5-phenoxysulfonyl-phenyl)-N',N''-bis-isobutoxycarbonyl-guanidine.

(b)
  N-(2-Propionamido-5-phenoxysulfonyl-phenyl)-N',N''-bis-methoxycarbonyl-guanidine
  N-(2-butyramido-5-phenoxysulfonyl-phenyl)-N',N''-bis-methoxycarbonylguanidine
  N-(2-iso-butyramido-5-phenoxysulfonyl-phenyl)-N',N''-bis-methoxycarbonyl-guanidine
  N-(2-valeramido-5-phenoxysulfonyl-phenyl)-N',N''-bis-methoxycarbonylguanidine
  N-(2-iso-valeramido-5-phenoxysulfonyl-phenyl)-N',N''-bis-methoxycarbonyl-guanidine
  N-(2-capronamido-5-phenoxysulfonyl-phenyl)-N',N''-bis-methoxy-carbonyl-guanidine
  N-(2-iso-capronamido-5-phenoxysulfonyl-phenyl)-N',N''-bis-methoxy-carbonyl-guanidine
  N-(2-methoxyacetamido-5-phenoxysulfonyl-phenyl)-N',N''-bis-methoxy-carbonyl-guanidine
  N-(2-cyclopentane-carbonamido-5-phenoxysulfonyl-phenyl)-N',N''-bismethoxy-carbonyl-guanidine
  N-(2-cyclohexane-carbonamido-5-phenoxysulfonyl-phenyl)-N',N''-bismethoxy-carbonyl-guanidine
  N-(2-phenylacetamido-5-phenoxysulfonyl-phenyl)-N',N''-bis-methoxy-carbonyl-guanidine
  N-(2-phenoxyacetamido-5-phenoxysulfonyl-phenyl)-N',N''-bis-methoxy-carbonyl-guanidine
  N-(2-benzamido-5-phenoxysulfonyl-phenyl)-N',N''-bis-methoxy-carbonyl-guanidine and their homologues corresponding to paragraph (a).

(c)
  N-(2-Acetamido-5-(4-chloro-phenoxysulfonyl-phenyl)-N',N''-bis-methoxy-carbonyl-guanidine
  N-(2-acetamido-5-(3-chloro-phenoxysulfonyl-phenyl)-N',N''-bis-methoxy-carbonyl-guanidine
  N-(2-acetamido-5-(2-chloro-phenoxysulfonyl-phenyl)-N',N''-bis-methoxy-carbonyl-guanidine
  N-(2-butyramido-5-(3-chloro-phenoxysulfonyl-phenyl)-N',N''-bis-methoxy-carbonyl-guanidine
  and their homologues corresponding to paragraphs (a) and (b).

(d)
  N-(2-Acetamido-5-(4-bromo-phenoxysulfonyl-phenyl)-N',N''-bis-methoxy-carbonyl-guanidine
  N-(2-acetamido-5-(4-methyl-phenoxysulfonyl-phenyl)-N',N''-bis-methoxy-carbonyl-guanidine
  N-(2-acetamido-5-(4-t.butyl-phenoxysulfonyl-phenyl)-N',N''-bis-methoxy-carbonyl-guanidine
  N-(2-acetamido-5-(4-methoxy-phenoxysulfonyl-phenyl)-N',N''-bis-methoxy-carbonyl-guanidine
  N-(2-acetamido-5-(4-ethoxy-phenoxysulfonyl-phenyl)-N',N''-bis-methoxy-carbonyl-guanidine
  N-(2-acetamido-5-(4-propoxy-phenoxysulfonyl-phenyl)-N',N''-bis-methoxy-carbonyl-guanidine
  N-(2-acetamido-5-(4-isopropoxy-phenoxysulfonyl-phenyl)-N',N''-bis-methoxy-carbonyl-guanidine
  N-(2-acetamido-5-(4-butoxy-phenoxysulfonyl-phenyl)-N',N''-bis-methoxy-carbonyl-guanidine
  N-(2-acetamido-5-(4-isobutoxy-phenoxysulfonyl-phenyl)-N',N''-bis-methoxy-carbonyl-guanidine
  N-(2-acetamido-5-(4-cyano-phenoxysulfonyl-phenyl)-N',N''-bis-methoxy-carbonyl-guanidine
  N-(2-acetamido-5-(3-methyl-phenoxysulfonyl-phenyl)-N',N''-bis-methoxy-carbonyl-guanidine
  N-(2-methoxyacetamido-5-(3-methyl-phenoxysulfonyl-phenyl)-N',N''-bis-methoxy-carbonyl-guanidine
  N-(2-butyramido-5-(3-methyl-phenoxysulfonyl-phenyl)-N',N''-bis-methoxy-carbonyl-guanidine
  and their position isomers corresponding to paragraph (c), as well as their homologues corresponding to paragraphs (a) and (b).

(e)
  N-(2-Acetamido-5-(3-trifluoromethyl-phenoxysulfonyl-phenyl)-N',N''-bis-methoxy-carbonyl-guanidine
  N-(2-acetamido-5-(3,5-bis-trifluoromethyl-phenoxysulfonyl-phenyl)-N',N''-bis-methoxy-carbonyl-guanidine
  N-(2-methoxyacetamido-5-(3-trifluoromethyl-phenoxysulfonyl-phenyl)-N',N''-bis-methoxy-carbonyl-guanidine
  N-(2-butyramido-5-(3-trifluoromethyl-phenoxysulfonyl-phenyl)-N',N''-bis-methoxy-carbonyl-guanidine and their homologues corresponding to paragraphs (a) and (b).

(f)

N-(2-Acetamido-5-(2-chloro-3-methyl-phenoxysulfonyl-phenyl)-N',N''-bvis-methoxycarbonyl-guanidine
N-(2-acetamido-5-(2-chloro-4-methyl-phenoxysulfonyl-phenyl)-N',N''-bis-methoxycarbonyl-guanidine
N-(2-acetamido-5-(2-chloro-5-methyl-phenoxysulfonyl-phenyl))-N',N''-bis-methoxycarbonyl-guanidine
N-(2-acetamido-5-(2-chloro-6-methyl-phenoxysulfonyl-phenyl)-N',N''-bis-methoxycarbonyl-guanidine
N-(2-acetamido-5-(3-chloro-2-methyl-phenoxysulfonyl-phenyl))-N',N''-bis-methoxycarbonyl-guanidine
N-(2-acetamido-5-(3-chloro-4-methyl-phenoxysulfonyl-phenyl))-N',N''-bis-methoxycarbonyl-guanidine
N-(2-acetamido-5-(3-chloro-5-methyl-phenoxysulfonyl-phenyl))-N',N''-bis-methoxycarbonyl-guanidine
N-(2-acetamido-5-(3-chloro-6-methyl-phenoxysulfonyl-phenyl))-N',N''-bis-methoxycarbonyl-guanidine
N-(2-acetamido-5-(4-chloro-2-methyl-phenoxysulfonyl-phenyl))-N',N''-bis-methoxycarbonyl-guanidine
N-(2-acetamido-5-(4-chloro-3-methyl-phenoxysulfonyl-phenyl))-N',N''-bis-methoxycarbonyl-guanidine and their homologues corresponding to paragraphs (a) and (b).

(g)
N-(2-Acetamido-5-(2,3-dichloro-phenoxysulfonyl-phenyl))-N',N''-bis-methoxycarbonyl-guanidine
N-(2-acetamido-5-(2,4-dichloro-phenoxysulfonyl-phenyl)-N',N''-bis-methoxycarbonyl-guanidine
N-(2-acetamido-5-(2,5-dichloro-phenoxysulfonyl-phenyl))-N',N''-bis-methoxycarbonyl-guanidine
N-(2-acetamido-5-(2,6-dichloro-phenoxysulfonyl-phenyl))-N',N''-bis-methoxycarbonyl-guanidine
N-(2-acetamido-5-(3,4-dichloro-phenoxysulfonyl-phenyl))-N',N''-bis-methoxycarbonyl-guanidine
N-(2-acetamido-5-(3,5-dichloro-phenoxysulfonyl-phenyl))-N',N''-bis-methoxycarbonyl-guanidine
and their homologues corresponding to paragraphs (a) and (b).

(h) N-(2-Acetamido-5-(2,3-dimethyl-phenoxysulfonyl-phenyl))-N',N''-bis-methoxycarbonyl-guanidine and their position isomers corresponding to paragraph (g) as well as their homologues corresponding to paragraphs (a) and (b).

Additions to paragraphs (c)
N-[2-Methoxyacetamido-5-(3-chloro-phenoxysulfonyl-phenyl)]-N',N''-bis-methoxycarbonyl-guanidine
N-[2-propionamido-5-(3-chloro-phenoxysulfonyl-phenyl)]-N',N''-bis-methoxycarbonyl-guanidine
N-[2-butyramido-5-(2-chloro-phenoxysulfonyl-phenyl)]-N',N''-bis-methoxycarbonyl-guanidine
and their homologues corresponding to paragraphs (a) and (b).

(d)
N-[2-Methoxyacetamido-5-(3-methyl-phenoxysulfonyl-phenyl)]-N',N''-bis-methoxycarbonyl-guanidine
N-[2-methoxyacetamido-5-(3-cyano-phenoxysulfonyl-phenyl)]-N',N''-bis-methoxycarbonyl-guanidine
N-[2-propionamido-5-(3-methyl-phenoxysulfonyl-phenyl)]-N',N''-bis-methoxycarbonyl-guanidine
N-[2-propionamido-5-(3-cyano-phenoxysulfonyl-phenyl)]-N',N''-bis-methoxycarbonyl-guanidine
N-[2-butyramido-5-(3-methyl-phenoxysulfonyl-phenyl)]-N',N''-bis-methoxy-carbonyl-guanidine
N-[2-butyramido-5-(3-cyano-phenoxysulfonyl-phenyl)]-N',N''-bis-methoxycarbonyl-guanidine
and their position isomers corresponding to paragraph (c).

(e)
N-[2-Methoxyacetamido-5-(3-trifluoromethyl-phenoxysulfonyl-phenyl)]-N',N''-bis-methoxycarbonyl-guanidine
N-[2-propionamido-5-(3-trifluoromethyl-phenoxysulfonyl-phenyl)]-N',N''-bis-methoxycarbonyl-guanidine
N-[2-butyramido-5-(3-trifluoromethyl-phenoxysulfonyl-phenyl)]-N',N''-bis-methoxycarbonyl-guanidine and their homologues corresponding to paragraphs (a) and (b).

(i)
N-(2-Acetamido-4-(4-methyl-phenoxysulfonyl-phenyl))-N',N''-bis-methoxycarbonyl-guanidine
N-(2-acetamido-4-(3-methyl-phenoxysulfonyl-phenyl))-N',N''-bis-methoxycarbonyl-guanidine
N-(2-acetamido-4-(3-chloro-phenoxysulfonyl-phenyl))-N',N''-bis-methoxycarbonyl-guanidine
N-(2-acetamido-4-(3-trifluoromethyl-phenoxysulfonyl-phenyl))-N',N''-bis-methoxycarbonyl-guanidine
N-(2-acetamido-4-(3-cyano-phenoxysulfonyl-phenyl))-N',N''-bis-methoxycarbonyl-guanidine
N-(2-methoxyacetamido-4-phenoxysulfonyl-phenyl)-N',N''-bis-methoxy-carbonyl-guanidine
N-(2-methoxyacetamido-4-(4-methyl-phenoxysulfonyl-phenyl))-N',N''-bis-methoxycarbonyl-guanidine
N-(2-methoxyacetamido-4-(3-methyl-phenoxysulfonyl-phenyl))-N',N''-bis-methoxycarbonyl-guanidine
N-(2-methoxyacetamido-4-(3-chloro-phenoxysulfonyl-phenyl))-N',N''-bis-methoxycarbonyl-guanidine
N-(2-methoxyacetamido-4-(3-trifluoromethyl-phenoxysulfonyl-phenyl))-N',N''-bis-methoxycarbonyl-guanidine
N-(2-methoxyacetamido-4-(3-cyano-phenoxysulfonyl-phenyl))-N',N''-bis-methoxycarbonyl-guanidine
N-(2-propionamido-4-phenoxysulfonyl-phenyl)-N',N''-bis-methoxy-carbonyl-guanidine
N-(2-propionamido-4-(4-methyl-phenoxysulfonyl-phenyl))-N',N''-bis-methoxycarbonyl-guanidine
N(2-propionamido-4-(3-methyl-phenoxysulfonyl-phenyl))-N',N''-bis-methoxycarbonyl-guanidine
N(2-propionamido-4-(3-chloro-phenoxysulfonyl-phenyl))-N',N''-bis-methoxycarbonyl-guanidine
N-(2-propionamido-4-(3-trifluoromethyl-phenoxysulfonyl-phenyl))-N',N''-bis-methoxycarbonyl-guanidine
N-(2-propionamido-4-(3-cyano-phenoxysulfonyl-phenyl))-N',N''-bis-methoxycarbonyl-guanidine
N-(2-butyramido-4-phenoxysulfonyl-phenyl)-N',N''-bis-methoxycarbonyl-guanidine
N-(2-butyramido-4-(4-methyl-phenoxysulfonyl-phenyl))-N',N''-bis-methoxycarbonyl-guanidine N-(2-butyramido-4-(3-methyl-phenoxysulfonyl-phenyl))-N',N''-bis-methoxycarbonyl-guanidine
N-(2-butyramido-4-(3-chloro-phenoxysulfonyl-phenyl))-N',N''-bis-methoxycarbonyl-guanidine
N-(2-butyramido-4-(3-trifluoromethyl-phenoxysulfonyl-phenyl))-N',N''-bis-methoxycarbonyl-guanidine
N-(2-butyramido-4-(3-cyano-phenoxysulfonyl-phenyl))-N',N''-bis-methoxycarbonyl-guanidine
N-(2-acetamido-4-phenoxysulfonyl-phenyl)-N',N''-bis-methoxycarbonyl-guanidine
and their analogues corresponding to paragraphs (a) through (h).

(k)
N-(2-Acetamido-5-(4-methyl-phenylsulfonyloxy-phenyl))-N',N''-bis-methoxycarbonyl-guanidine
N-(2-acetamido-5-(3-methyl-phenylsulfonyloxy-phenyl))-N',N''-bis-methoxycarbonyl-guanidine
N-(2-acetamido-5-(3-chloro-phenylsulfonyloxy-phenyl))-N',N''-bis-methoxycarbonyl-guanidine
N-(2-acetamido-5-(3-trilfuoromethyl-phenylsulfonyloxy-phenyl))-N', N'''-bis-methoxycarbonyl-guanidine
N-(2-acetamido-5-(3-cyano-phenylsulfonyloxy-phenyl))-N'N''-bis methoxycarbonyl-guanidine
N-(2-methoxyacetamido-5-phenylsulfonyloxy-phenyl)-N'N''-bis-methoxycarbonyl-guanidine
N-(2-methoxyacetamido-5-(4-methyl-phenylsulfonyloxy-phenyl))-N', N''-bis-methoxycarbonyl-guanidine
N-(2-methoxyacetamido-5-(3-methyl-phenylsulfonyloxy-phenyl))-N', N''-bis-methoxycarbonyl-guanidine
N-(2-methoxyacetamido-5-(3-chloro-phenylsulfonyloxy-phenyl))-N', N''-bis-methoxycarbonyl-guanidine
N-(2-methoxyacetamido-5-(3-trifluoromethyl-phenylsulfonyloxy-phenyl))-N',N''-bis-methoxycarbonyl-guanidine
N-(2-methoxyacetamido-5-(3-cyano-phenylsulfonyloxy-phenyl))-N',N''-bis-methoxycarbonyl-guanidine
N-(2-propionamido-5-phenylsulfonyloxy-phenyl)-N',N''-bis-methoxycarbonyl-guanidine
N-(2-propionamido-5-(4-methyl-phenylsulfonyloxy-phenyl))-N',N''-bis-methoxycarbonyl-guanidine
N-(2-propionamido-5-(3-methyl-phenylsulfonyloxy-phenyl))-N',N''-bis-methoxycarbonyl-guanidine
N-(2-propionamido-5-(3-chloro-phenylsulfonyloxy-phenyl))-N',N''-bis-methoxycarbonyl-guanidine
N-(2-propionamido-5-(3-trifluoromethyl-phenylsulfonyloxy-phenyl))-N',N''-bis-methoxycarbonyl-guanidine
N-(2-propionamido-5-(3-cyano-phenylsulfonyloxy-phenyl))-N',N''-bis-methoxycarbonyl-guanidine
N-(2-butyramido-5-phenylsulfonyloxy-phenyl)-N',N''-bis-methoxycarbonyl-guanidine
N-(2-butyramido-5-(4-methyl-phenylsulfonyloxy-phenyl))-N',N''-bis-methoxycarbonyl-guanidine
N-(2-butyramido-5-(3-methyl-phenylsulfonyloxy-phenyl))-N',N''-bis-methoxycarbonyl-guanidine
N-(2-butyramido-5-(3-chloro-phenylsulfonyloxy-phenyl))-N',N''-bis methoxycarbonyl-guanidine
N-(2-butyramido-5-(3-trifluoromethyl-phenylsulfonyloxy-phenyl))-N', N''-bis-methoxycarbonyl-guanidine
N-(2-butyramido-5-(3-cyano-phenylsulfonyloxy-phenyl))-N',N''-bis-methoxycarbonyl-guanidine
N-(2-acetamido-5-phenylsulfonyloxy-phenyl)-N',N''-bis-methoxycarbonyl-guanidine
and their analogues corresponding to paragraphs (a) through (i).

(l)
N-(2-Acetamido-4-(4-methyl-phenylsulfonyloxy-phenyl))-N',N''-bis-methoxycarbonyl-guanidine
N-(2-acetamido-4-(3-methyl-phenylsulfonyloxy-phenyl))-N',N''-bis-methoxycarbonyl-guanidine
N-(2-acetamido-4-(3-chloro-phenylsulfonyloxy-phenyl))-N',N''-bis-methoxycarbonyl-guanidine
N-(2-acetamido-4-(3-trifluoromethyl-phenylsulfonyloxy-phenyl))-N', N''-bis-methoxycarbonyl-guanidine
N-(2-acetamido-4-(3-cyano-phenylsulfonyloxy-phenyl))-N',N''-bis methoxycarbonyl-guanidine
N-(2-methoxyacetamido-4-phenylsulfonyloxy-phenyl)-N',N''-bis-methoxycarbonyl-guanidine
N-(2-methoxyacetamido-4-(4-methyl-phenylsulfonyloxy-pheny))-N',N''-bis-methoxycarbonyl-guanidine
N-(2-methoxyacetamido-4-(3-methyl-phenylsulfonyloxy-phenyl))N',N''-bis-methoxycarbonyl-guanidine
N-(2-methoxyacetamido-4-(3-chloro-phenylsulfonyloxy-phenyl))-N',N''-bis-methoxycarbonyl-guanidine
N-(2-methoxyacetamido-4-(3-trifluoromethyl-phenylsulfonyloxy-phenyl))-N',N''-bis-methoxycarbonyl-guanidine
N-(2-methoxyacetamido-4-(3-cyano-phenylsulfonyloxy-phenyl))-N',N''-bis-methoxycarbonyl-guanidine
N-(2-propionamido-4-phenylsulfonyloxy-phenyl))-N',N''-bis-methoxycarbonyl-guanidine
N-(2-propionamido-4-(4-methyl-phenylsulfonyloxy-phenyl))-N',N''-bis-methoxycarbonyl-guanidine
N-(2-propionamido-4-(3-methyl-phenylsulfonyloxy-phenyl))-N',N''-bis-methoxycarbonyl-guanidine
N-(2-propionamido-4-(3-chloro-phenylsulfonyloxy-phenyl))-N',N''-methoxycarbonyl-guanidine
N-(2-propionamido-4-(3-trifluoromethyl-phenylsulfonyloxy-phenyl-N',N''-bis-methoxycarbonyl-guanidine
N-(2-propionamido-4-(3-cyano-phenylsulfonyloxy-phenyl))-N',N''-bis-methoxycarbonyl-guanidine
N-(2-butyramido-4-phenylsulfonyloxy-phenyl)-N',N''-bis-methoxycarbonyl-guanidine
N-(2-butyramido-4-(4-methyl-phenylsulfonyloxy-phenyl))-N',N''-bis-methoxycarbonyl-guanidine
N-(2-butyramido-4-(3-methyl-phenylsulfonyloxy-phenyl))-N',N''-bis-methoxycarbonyl-guanidine
N-(2-butyramido-4-(3-chloro-phenylsulfonyloxy-phenyl))-N',N''-bis-methoxycarbonyl-guanidine
N-(2-butyramido-4-(3-trifluoromethyl-phenylsulfonyloxy-phenyl))N', N''-bis-methoxycarbonyl-guanidine
N-(2-butyramido-4-(3-cyano-phenylsulfonyloxy-phenyl))-N',N''-bis-methoxycarbonyl-guanidine
N-(2-acetamido-4-phenylsulfonyloxy-phenyl)-N',N''-bis-methoxycarbonyl-guanidine
and their analogues corresponding to paragraphs (a) through (i).

(m)
N-(2-$N^2$-Methylureido)-5-phenoxysulfonyl-phenyl)-N',N''-bis-methoxycarbonyl-guanidine
N-(2-($N^2$-ethylureido)-5-phenoxysulfonyl-phenyl)-N',N''-bis-methoxycarbonyl-guanidine N-(2-($N^2$-butylureido)-5-phenoxysulfonyl-phenyl)-N',N''-bis-methoxycarbonyl-guanidine N-(2-$N^2$-ω-cyanopentylureido)-5-phenoxysulfonyl-phenyl)-N',N''-bis methoxycarbonyl-guanidine N-(2-($N^2$-β-methoxyethylureido)-5-phenoxysulfonyl-phenyl)-N',N''-bis-methoxycarbonyl-guanidine N-(2-($N^2$-benzylureido)-5-phenoxysulfonyl-phenyl)-N',N''-bis-methoxycarbonyl-guanidine N-(2-($N^2$-phenylureido)-5-phenoxysulfonyl-phenyl)-N',N''-bis-methoxycarbonyl-guanidine and their analogues corresponding to paragraphs (a) through (l).

(n)

N-(2-Acetamino-5-phenylsulfonyl-phenyl)-N'-methoxycarbonyl-N''-acetyl-guanidine

N-(2-acetamino-5-phenoxysulfonyl-phenyl)-N'-methoxycarbonyl-N''-propionyl-guanidine N-(2-acetamino-5-phenoxysulfonyl-phenyl)-N'-methoxycarbonyl-N''-butyryl-guanidine N-(2-acetamino-5-phenoxysulfonyl-phenyl)-N'-methoxycarbonyl-N''-cyclohexane-carbonyl-guanidine N-(2-acetamino-5-phenoxysulfonyl-phenyl)-N'-methoxycarbonyl-N''-benzoyl-guanidine N-(2-acetamino-5-phenoxysulfonyl)-phenyl-N'-methoxycarbonyl-N''-phenacetyl-guanidine N-(2-acetamino-5-phenoxysulfonyl-phenyl)-N'-methoxycarbonyl-N''-phenoxyacetyl-guanidine and their analogues corresponding to paragraphs (a) through (m).

(o)

N-(2-Acetamino-5-phenoxysulfonyl-phenyl)-N'-ethoxycarbonyl-N''-acetyl-guanidine

N-(2-acetamino-5-phenoxysulfonyl-phenyl)-N'-propoxycarbonyl-N''-acetyl-guanidine N-(2-acetamino-5-phenoxysulfonyl-phenyl)-N'-iso-propoxycarbonyl-N''-acetyl-guanidine N-(2-acetamino-5-phenoxysulfonyl-phenyl)-N'-butoxycarbonyl-N''-acetyl-guanidine N-(2-acetamino-5-phenoxysulfonyl-phenyl)-N'-isobutoxycarbonyl-N''-acetyl-guanidine and their analogues corresponding to paragraphs (a) through (n).

The novel substituted phenylguanidines of the invention are valuable chemotherapeutical agents and are suitable for the treatment of parasitic diseases in mammals, such as those caused by helminths and liver flukes. They are especially active against a great number of helminths, for example, Haemonchus, Trichostrongylus, Ostertagia, Strongyloides, Cooperia, Chabertia, Oesophagostomum, Hyostrongulus, Ankylostoma, Askaris and Heterakis, and Fasciola. Their action is particularly pronounced against gastro-intestinal strongylides and liver flukes, which attack above all ruminants. Therefore the compounds according to the invention are used especially in veterinary preparations.

Depending on the case, the compounds of the formula I are administered in doses of from 0.5 to 50 mg per kg of body weight for 1 to 14 days.

For oral application there are mentioned tablets, dragees, capsules, powders, granules or pastes which contain the active ingredients together with the common auxiliary agents or carriers, such as starch, cellulose powder, talc, magnesium stearate, sugar, gelatin, calcium carbonate, finely divided silicic acid, carboxymethyl cellulose or similar substances.

The products of the invention process show an excellent effectiveness not only when applied orally, but also parenterally.

For parenteral application there are mentioned solutions, for example, oily solutions which are prepared using sesame oil, castor oil or synthetic triglycerides, optionally with the addition of tocopherol as anti-oxidant agent and/or using surfactants, such as sorbitan-fatty acid-ester. Besides, there are mentioned aqueous suspensions which are prepared using ethoxylated sorbitan-fatty acid-esters, optionally with the addition of thickening agents, such as polyethylene-glycol or carboxymethyl cellulose.

The concentration of the active ingredients of the invention in the compositions prepared with them is preferably in the range of from 2 to 20% by weight for the use as veterinary preparation; for human use, it is preferably between 20 and 80% by weight.

The products of the invention process are especially active against liver flukes. Thus, the products of Examples 5.2, 5.3 and 6.30 show an action of more than 90% with an oral application of 10 mg/kg. The action against gastro-intestinal nematodes is also very good, for example, the product of Example 4.1 shows an action of 90% with a subcutaneous application of 2.5 mg/kg.

The following Examples serve to illustrate the invention.

Examples of Preparation

EXAMPLE 1.1

37 Grams of 2-amino-4-phenoxysulfonyl-acetanilide are refluxed in 250 ml of methanol with 25 g of N,N'-bis-methoxycarbonylisothio-urea-S-methyl ether and 0.01 g of p-toluenesulfonic acid for 5 hours. Subsequently the solvent is distilled off under reduced pressure, and the residue is stirred with ethyl acetate. The crystallized N-(2-acetamino-5-phenoxy-sulfonyl-phenyl)-N',N''-bis-methoxycarbonyl-guanidine is filtered off and washed with ethyl acetate and methanol. Yield 13 g. Melting point 190° C. (decomposition).

For the preparation of the 2-amino-4-phenoxysulfonyl-acetanilide, 40 g of 2-nitro-4-phenoxysulfonyl-acetanilide in 500 ml of methanol are hydrogenated with Raney nickel under normal pressure. The solution is filtered off from the catalyst, and the filrate is concentrated under reduced pressure. The residue can be processed directly as indicated above, without further purification. The yield of 2-amino-4-phenoxysulfonyl-acetanilide is 32 g. Melting point from methanol 130° C.

For the preparation of the 2-nitro-4-phenoxysulfonyl-acetanilide, 50 g of 2-nitro-4-phenoxysulfonyl-aniline in 250 ml of acetanhydride are mixed, while stirring, with 1 ml of concentrated $H_2SO_4$, the reaction mixture being heated in the process. The stirring is continued for another 2 hours, and the mixture is then concentrated under reduced pressure. Diisopropyl ether is added to the solid residue, and the crystallized 2-nitro-4-phenoxysulfonyl-acetanilide is filtered off with suction. Yield 40 g. Melting point from methanol 124° C.

For the preparation of the 2-nitro-4-phenoxysulfonylaniline, 54 g of 2-nitro-4-phenoxysulfonyl-chlorobenzene in 500 ml of dioxan are kept in an autoclave with gaseous ammonia at 50° C. and 5 atmospheres gage for 5 hours, and thereafter the solvent is distilled off under reduced pressure. 200 Milliliters of a mixture of equal parts of methanol and water are added to the residue. After a short time the 2-nitro-4-phenoxysulfonyl-aniline precipitates in the form of crystals. The raw product is purified from methanol and then from benzene. Yield 28 g. M.p. 104° C.

For the preparation of the 2-nitro-4-phenoxysulfonyl-chlorobenzene, 51 g of 3-nitro-4-chloro-benzene-sulfonic acid chloride in 120 ml of acetone are mixed with 18.8 g of phenol, and 28 ml of triethylamine are added dropwise under cooling at an internal temperature not exceeding 10° C. After stirring the mixture for several hours at room temperature, it is mixed with water, in which process an oil separates which is then worked up over ether. The yield of 2-nitro-4-phenoxy-sulfonyl-chlorobenzene is 54 g. Melting point from methanol 71° C.

In an analogous manner, there are prepared from 2-amino-4-phenoxysulfonyl-acetanilide and 1.2 N,N'-bis-ethoxycarbonyl-isothio-urea-S-methylether, the N-(2-acetamido-5-phenoxysulfonyl-phenyl)-N',N''-bis-ethoxycarbonylguanidine 1.3 N,N-bis-propoxycarbonyl-isothio-urea-S-methylether, the N-(2-acetamido-5-phenoxysulfonyl-phenyl)-N',N''-bis-propoxycarbonyl-guanidine 1.4 N,N'-bis-isopropoxycarbonyl-isothio-urea-S-methylether, the N-(2-acetamido-5-phenoxysulfonyl-phenyl)-N',N''-bis-isopropoxycarbonyl-guanidine 1.5 N,N'-bis-butoxycarbonyl-isothio-urea-S-methylether, the N-(2-acetamido-5-phenoxysulfonyl-phenyl-N',N''-bis-butoxycarbonyl-guanidine 1.6 N,N'-bis-isobutoxycarbonyl-isothio-urea-S-methylether, the N-(2-acetamido-5-phenoxysulfonyl-phenyl)-N',N''-bis-isobutoxycarbonyl-guanidine 1.7 N-methoxycarbonyl-N'-propionyl-isothio-urea-S-methylether, the N-(2-acetamido-5-phenoxysulfonyl-phenyl)-N'-methoxycarbonyl-N''-propionyl-guanidine 1.8 N-ethoxycarbonyl-N'-benzoyl-isothio-urea-S-methylether, the N-(2-acetamido-5-penoxysulfonyl-phenyl)-N'-ethoxycarbonyl-N''-benzoyl-guanidine 1.9 N-methoxycarbonyl-N'-cyclohexylcarbonyl-isothio-urea-S-methylether, the N-(2-acetamido-5-phenoxysulfonyl-phenyl)-N'-methoxycarbonyl-N''-cyclohexylcarbonyl-guanidine 1.10 N-methoxycarbonyl-N'-ethoxymethylcarbonyl-isothio-urea-S-methylether, the N-(2-acetamido-5-phenoxysulfonyl-phenyl)-N'-methoxycarbonyl-N''-ethoxymethylcarbonyl-guanidine.

EXAMPLE 2.1

According to Example 1, 27 g of 2-amino-4-phenoxysulfonylbutyranilide are reacted with 20 g of N,N'-bis-methoxycarbonylisothio-urea-S-methylether, and 9 g of N-(2-butyramido-5-phenoxysulfonyl-phenyl)-N',N''-bis-methoxycarbonyl-guanidine are obtained.

For the preparation of the 2-amino-4-phenoxysulfonylbutyranilide, 14 ml of butyrylchloride are added dropwise to 29.6 g of 2-nitro-4-phenoxysulfonyl-aniline, m.p. 104° C., in 300 ml of toluene at 100° C., while stirring, the mixture being kept under reflux for 2 hours. Subsequently the solution is concentrated under reduced pressure, and diisopropylether is added to the residue. The precipitated 2-nitro-4-phenoxysulfonyl-butyranilide is filtered off, washed with diisopropyl ether and hydrogenated according to Example 1, to give 2-amino-4-phenoxysulfonyl-butyranilide.

In an analogous manner, the following products are prepared, while using starting compounds that have been modified accordingly.

While using starting compounds accordingly modified, the following products are obtained in a manner analogous to that of Example 1 from

| | Step 1 | Step 2 | Product of the invention |
|---|---|---|---|
| | R—COCl | structure with OSO₂, NO₂, NH—CO—R | structure with OSO₂, NH—CO—R, N=C(N—COOCH₃)(NHCOOCH₃) |

| Bsp. | R |
|---|---|
| 2.2 | —CH₂OCH₃ |
| 2.3 | —C₂H₅ |
| 2.4 | —i-C₃H₇ |
| 2.5 | —C₄H₉ |
| 2.6 | —i-C₄H₉ |
| 2.7 | —C₅H₁₁ |
| 2.8 | —i-C₅H₁₁ |
| 2.9 | (cyclopentyl) |
| | (cyclohexyl) |
| 2.10 | |
| 2.11 | —CH₂—C₆H₅ |
| 2.12 | —CH₂—O—C₆H₅ |
| 2.13 | —CO—C₆H₅ |

| | Step 1 | | Step 2 | | Step 3 | | Step 4 | | Product of the invention | | |
|---|---|---|---|---|---|---|---|---|---|---|---|
| Bsp. | R | M.P. °C. | R | M.P. °C. | R¹ | M.P. °C. | | M.P. °C. | R² | | |
| 3.1 | 4-Cl | 84 | | 156 | CH₃ | | | | COOCH₃ | COOCH₃ | |
| 3.2 | 3-Cl | 68 | | 138 | CH₃ | | | | COOCH₃ | COOCH₃ | |
| 3.3 | 3-Cl | | | | CH₃ | | | | COOC₂H₅ | COOC₂H₅ | |
| 3.4 | 3-Cl | | | | CH₃ | | | | COOC₃H₇ | COOC₃H₇ | |
| 3.5 | 3-Cl | | | | CH₃ | | | | COOCH₃ | COOC₂H₅ | |
| 3.6 | 3-Cl | | | | CH₃ | | | | COOCH₃ | COOC₆H₁₁ | |
| 3.7 | 3-Cl | | | | CH₃ | | | | COOCH₃ | COC₂H₅ | |
| 3.8 | 3-Cl | | | | CH₃ | | | | COOCH₃ | COCH₂OC₂H₅ | |
| 3.9 | 3-Cl | | | | CH₃ | | | | COOCH₂CH=CH₂ | COOCH₃ | |
| 3.10 | 3-Cl | | | | C₃H₇ | | | | COOCH₃ | COOCH₃ | |
| 3.11 | 3-Cl | | | | CH₂OCH₃ | | | | COOCH₃ | COOCH₃ | |
| 3.12 | 2-Cl | | | | C₃H₇ | | | | COOCH₃ | COOCH₃ | |
| 3.13 | 2,5-Cl | | | | CH₃ | | | | COOCH₃ | COOCH₃ | |
| 3.14 | 3,5-Cl | 104 | | 164 | C₃H₇ | | | | COOCH₃ | COOCH₃ | |

-continued

| Ex. | R | M.P. °C | R¹ | M.P. °C | M.P. °C | R² | R³ | M.P. °C |
|---|---|---|---|---|---|---|---|---|
| 3.15 | 4-Br | | C₂H₅ | | COOCH₃ | COOCH₃ | COOCH₃ | |
| 3.16 | 3-Br | 72 | C₃H₇ | 141 | | COOCH₃ | COOCH₃ | |
| 3.17 | 3-Br | | CH₂OCH₃ | | | COOCH₃ | COOCH₃ | |
| 3.18 | 3-Br | | CH₃ | | | COOCH₃ | COOCH₃ | |
| 3.19 | 2-Br | | CH₃ | | | COOCH₃ | COOCH₃ | |
| 3.20 | 4-CH₃ | 68 | CH₃ | 135 | | COOCH₃ | COOCH₃ | |
| 3.21 | 3-CH₃ | 60 | C₂H₅ | 138 | | COOCH₃ | COOCH₃ | |
| 3.22 | 3-CH₃ | | C₃H₇ | | | COOCH₃ | COOCH₃ | |
| 3.23 | 3-CH₃ | | CH₂OCH₃ | | | COOCH₃ | COOCH₃ | |
| 3.24 | 2-CH₃ | | CH₃ | | | COOCH₃ | COOCH₃ | |
| 3.25 | 4-t.Bu | | CH₃ | | | COOCH₃ | COOCH₃ | |
| 3.26 | 2,4-CH₃ | | CH₃ | | | COOCH₃ | COOCH₃ | |
| 3.27 | 2-Cl-4-CH₃ | | CH₃ | | | COOCH₃ | COOCH₃ | |
| 3.28 | 3,5-Cl | | CH₂OCH₃ | 132 | | COOCH₃ | COOCH₃ | |
| 3.29 | 3-CF₃ | 65 | C₂H₅ | | | COOCH₃ | COOCH₃ | |
| 3.30 | 3-CH₃ | | C₃H₇ | | | COOCH₃ | COOCH₃ | |
| 3.31 | 3-CF₃ | | C₃H₇ | 93 | (oil) | COOC₂H₅ | COOCH₃ | |
| 3.32 | 3-CF₃ | | C₃H₇ | | | COOCH₃ | COC₂H₅ | |
| 3.33 | 3-CF₃ | | C₃H₇ | | | COOCH₃ | COOCH₂CH=CH₂ | |
| 3.34 | 3-CF₃ | | C₃H₇ | | | COOCH₃ | COOCH₂C≡CH | 163 |
| 3.35 | 3-CF₃ | 88 | CH₃ | 140 | | COOCH₃ | COOCH₃ | |
| 3.36 | 4-OCH₃ | (oil) | CH₃ | 116 | | COOCH₃ | COOCH₃ | |
| 3.37 | 3-OCH₃ | (oil) | CH₃ | 86 | | COOCH₃ | COOCH₃ | |
| 3.38 | 3-OC₂H₅ | 118 | CH₃ | 183 | | COOCH₃ | COOCH₃ | |
| 3.39 | 3-CN | | CH₃ | | | COOCH₃ | COOCH₃ | |
| 3.40 | 3-CN | | C₂H₅ | | | COOCH₃ | COOCH₃ | |
| 3.41 | 3-CN | | C₃H₇ | | | COOCH₃ | COOCH₃ | |
| 3.42 | 3-CN | | CH₂OCH₃ | | | COOCH₃ | COOCH₃ | |
| 3.43 | 3-CN | | | | | COOCH₃ | COOCH₃ | |

EXAMPLE 4.1

34 Grams of 2-amino-phenylsulfonyloxy-acetanilide are heated for 5 hours under reflux in 200 ml of methanol with 40 g of N,N'-bis-methoxycarbonyl-isothio-urea-S-methylether and 0.01 g of p-toluene-sulfonic acid. Subsequently the solvent is distilled off under reduced pressure and the residue is stirred with ethyl acetate. The crystallized N-(2-acetamido-5-phenylsulfonyloxy-phenyl)-N'-N''-bis-methoxycarbonyl-guanidine is filtered off and washed with ethyl acetate and methanol. Yield 35 g. Melting point 181° C. (decomposition).

For the preparation of the 2-amino-4-phenylsulfonyloxy-acetanilide, 50 g of 2-nitro-4-phenylsulfonyloxy-acetanilide in 250 ml of methanol are hydrogenated in the presence of Raney nickel under normal pressure at room temperature. The catalyst is filtered off, washed with dimethylformamide, and the filtrate in concentrated under reduced pressure. The remaining 2-amino-4-phenylsulfonyloxy-acetanilide is pure enough for further processing. Yield 44 g. Melting point from methanol 154° C.

For the preparation of the 2-nitro-4-phenylsulfonyloxy-acetanilide, 48 g of 2-nitro-4-phenylsulfonyloxy-aniline in 250 ml of acetanhydride are mixed, while stirring, with 1 ml of concentrated $H_2SO_4$, in which process the reaction mixture is heated. The stirring is continued for another 2 hours, and the mixture is then concentrated under reduced pressure. The oily residue is worked up over ethyl acetate, and a solid residue of 2-nitro-4-phenylsulfonyloxy-acetanilide is obtained. It is dissolved in 100 ml of hot methanol for purification and diluted with 100 ml of water. After cooling, the 2-nitro-4-phenylsulfonyloxy-acetanilide is filtered off and washed with water. Yield 52 g. Melting point from methanol 98° C.

For the preparation of the 2-nitro-4-phenylsulfonyloxy-aniline, 15.4 g of 3-nitro-4-amino-phenol in 100 ml of acetone are mixed with 14 ml of triethylamine, and a solution of 17.6 g of benzene-sulfonic acid chloride in 30 ml of acetone is added dropwise, while stirring, at a temperature not exceeding 20° C., in an ice bath. After 3 hours of stirring, the reaction solution is filtered off from the triethylamine hydrochloride, and the filtrate is evaporated to dryness. It is thereafter stirred with 50 ml of methanol, and the precipitated 2-nitro-4-phenyl-sulfonyloxy-aniline is filtered off and washed with methanol. Yield 18 g. M.p. from methanol 140° C.

In an analogous manner, there are prepared from 2-amino-4-phenylsulfonyloxy-acetanilide and 4.2     N,N'-bis-ethoxycarbonyl-isothio-urea-S-methylether, the N-(2-acetamido-5-phenylsulfonyloxy-phenyl)-N',N''-bis-ethoxycarbonyl-guanidine 4.3     N,N'-bis-propoxycarbonyl-isothio-urea-S-methylether, the N-(2-acetamido-5-phenylsulfonyloxy-phenyl)-N',N''-bis-propoxycarbonyl-guanidine 4.4     N,N'-bis-isopropoxycarbonyl-isothio-urea-S-methylether, the N-(2-acetamido-5-phenylsulfonyloxy-phenyl)-N',N''-bis-isopropoxycarbonyl-guanidine 4.5     N,N'-bis-butoxycarbonyl-isothio-urea-S-methylether, the N-(2-acetamido-5-phenylsulfonyloxy-phenyl)-N',N''-bis-butoxycarbonyl-guanidine 4.6     N,N'-bis-isobutoxycarbonyl-isothio-urea-S-methylether, the N-(2-acetamido-5-phenylsulfonyloxy-phenyl)-N',N''-bis-isobutoxycarbonyl-guanidine 4.7     N-methoxycarbonyl-N'-propionyl-urea-S-methylether, the N-(2-acetamido-5-phenylsulfonyloxy-phenyl)-N'-methoxycarbonyl-N''-propionyl-guanidine 4.8     N-ethoxycarbonyl-N'-benzoyl-isothio-urea-S-methylether, the N-(2-acetamido-5-phenylsulfonyloxy-phenyl)-N'-ethoxycarbonyl-N''-benzoyl-guanidine 4.9     N-methoxycarbonyl-N'-cyclohexylcarbonyl-isothio-urea-S-methylether, the N-(2-acetamido-5-phenylsulfonyloxy-phenyl)-N'-methoxycarbonyl-N''-cyclohexylcarbonyl-guanidine 4.10 N-methoxycarbonyl-N'-ethoxymethylcarbonyl-isothio-urea-S-methylether, the N-(2-acetamido-5-phenylsulfonyloxy-phenyl)-N'-methoxycarbonyl-N''-ethoxymethylcarbonyl-guanidine

EXAMPLE 5.1

In a manner analogous to that of Example 4, 27 g of 2-amino-4-phenyl-sulfonyloxy-butyranilide are reacted with 20 g of N,N'-bis-methoxycarbonyl-isothio-urea-S-methylether, and 9 g of N-(2-butyramido-5-phenylsulfonyloxy-phenyl)-N',N''-bis-methoxycarbonyl-guanidine, m.p. 158° C., are obtained.

For the preparation of the 2-amino-4-phenylsulfonyloxy-butyranilide, 14 ml of butyrylchloride are added dropwise to 29.6 g of 2-nitro-4-phenylsulfonyloxy-aniline, m.p. 148° C., in 300 ml of toluene, while stirring at 100° C., and the mixture is kept under reflux for 2 hours. Thereafter the solution is concentrated under reduced pressure, and the residue is mixed with diisopropylether. The precipitated 2-nitro-4-phenylsulfonyloxy-butyranilide, m.p. 58° C., is filtered off, washed with diisopropylether and hydrogenated according to Example 4, to give 2-amino-4-phenylsulfonyloxy-butyranilide, m.p. 89° C.

While using starting compounds accordingly modified, the following products are obtained in a manner analogous to that of Example 4.1 from

| Ex. | Step 1 (NO$_2$, NH—CO—R on phenyl-SO$_2$O-phenyl) | | Step 2 (NH$_2$, NH—CO—R) | | Product of the invention | |
|---|---|---|---|---|---|---|
| | R | M.P. °C. | | M.P. °C. | | M.P. °C. |
| 5.2 | —CH$_2$OCH$_3$ | 108 | | 150 | | 130 |
| 5.3 | —C$_2$H$_5$ | 87 | | 147 | | 139 |
| 5.4 | -i-C$_3$H$_7$ | | | | | |
| 5.5 | —C$_4$H$_9$ | | | | | |
| 5.6 | -i-C$_4$H$_9$ | | | | | |
| 5.7 | —C$_5$H$_{11}$ | | | | | |
| 5.8 | -i-C$_5$H$_{11}$ | | | | | |
| 5.9 | | | | | | |
| 5.10 | cyclopentyl | 103 | | 180 | | 164 |
| 5.11 | —CH$_2$—C$_6$H$_5$ | | | | | |
| 5.12 | —CH$_2$—O—C$_6$H$_5$ | | | | | |
| 5.13 | —CO—C$_6$H$_5$ | | | | | |

| Ex. | Step 1 | | Step 2 | | Step 3 | | Product of the invention | | | |
|---|---|---|---|---|---|---|---|---|---|---|
| | R | M.P. °C. | R$^1$ | M.P. °C. | | M.P. °C. | R$^2$ | R$^3$ | | M.P. |
| 6.1 | 4-Cl | 137 | CH$_3$ | | | | COOCH$_3$ | COOCH$_3$ | | |
| 6.2 | 3-Cl | 154 | CH$_3$ | | | | COOCH$_3$ | COOC$_2$H$_5$ | | |
| 6.3 | 3-Cl | | CH$_3$ | | | | COOC$_2$H$_5$ | COOC$_2$H$_5$ | | |
| 6.4 | 3-Cl | | CH$_3$ | | | | COOC$_3$H$_7$ | COOC$_3$H$_7$ | | |
| 6.5 | 3-Cl | | CH$_3$ | | | | COOCH$_3$ | COOC$_2$H$_5$ | | |
| 6.6 | 3-Cl | | CH$_3$ | | | | COOCH$_3$ | COOC$_6$H$_{11}$ | | |
| 6.7 | 3-Cl | | CH$_3$ | | | | COOCH$_3$ | COOC$_2$H$_5$ | | |
| 6.8 | 3-Cl | | CH$_3$ | | | | COOCH$_3$ | COC$_6$H$_5$ | | |
| 6.9 | 3-Cl | | CH$_3$ | | | | COOCH$_3$ | COCH$_2$OC$_2$H$_5$ | | |
| 6.10 | 3-Cl | | C$_3$H$_7$ | | | | COOCH$_2$CH=CH$_2$ | COOCH$_3$ | | |
| 6.11 | 3-Cl | | CH$_2$OCH$_3$ | | | | COOCH$_3$ | COOCH$_3$ | | |
| 6.12 | 2-Cl | | C$_3$H$_7$ | | | | COOCH$_3$ | COOCH$_3$ | | |
| 6.13 | 2,5-Cl | | CH$_3$ | | | | COOCH$_3$ | COOCH$_3$ | | |
| 6.14 | 3,5-Cl | 170 | C$_3$H$_7$ | | | | COOCH$_3$ | COOCH$_3$ | | |

-continued

| Ex. | R | M.P. °C. | R¹ | M.P. °C. | M.P. °C. | R² | R³ | M.P. °C. |
|---|---|---|---|---|---|---|---|---|
| 6.15 | 4-Br | | CH₃ | | | COOCH₃ | COOCH₃ | |
| 6.16 | 3-Br | 158 | C₂H₅ | | | COOCH₃ | COOCH₃ | |
| 6.17 | 3-Br | | C₃H₇ | | | COOCH₃ | COOCH₃ | |
| 6.18 | 3-Br | | CH₂OCH₃ | | | COOCH₃ | COOCH₃ | |
| 6.19 | 2-Br | | CH₃ | | | COOCH₃ | COOCH₃ | |
| 6.20 | 4-CH₃ | 149 | CH₃ | | | COOCH₃ | COOCH₃ | |
| 6.21 | 3-CH₃ | 142 | CH₃ | | | COOCH₃ | COOCH₃ | |
| 6.22 | 3-CH₃ | | C₂H₅ | | | COOCH₃ | COOCH₃ | |
| 6.23 | 3-CH₃ | | C₃H₇ | | | COOCH₃ | COOCH₃ | |
| 6.24 | 3-CH₃ | | CH₂OCH₃ | | | COOCH₃ | COOCH₃ | |
| 6.25 | 2-CH₃ | | CH₃ | | | COOCH₃ | COOCH₃ | |
| 6.26 | 4-t.Bu | | CH₃ | | | COOCH₃ | COOCH₃ | |
| 6.27 | 2,4-CH₃ | | CH₃ | | | COOCH₃ | COOCH₃ | |
| 6.28 | 2-Cl-4-CH₃ | | CH₃ | | | COOCH₃ | COOCH₃ | |
| 6.29 | 3,4-Cl | 149 | CH₃ | | | COOCH₃ | COOCH₃ | |
| 6.30 | 3-CF₃ | 131 | CH₃ | | | COOCH₃ | COOCH₃ | 185 |
| 6.31 | 3-CF₃ | 131 | CH₂OCH₃ | 151 | 106 | COOCH₃ | COOCH₃ | 129 |
| 6.32 | 3-CF₃ | | C₂H₅ | 116 | Resin | COOCH₃ | COOCH₃ | 180 |
| 6.33 | 3-CF₃ | | C₃H₇ | 146 | 112 | COOCH₃ | COOCH₃ | 163 |
| 6.34 | 3-CF₃ | | C₃H₇ | 100 | 90 | COOCH₃ | COOCH₃ | |
| 6.35 | 3-CF₃ | | C₃H₇ | | | COOC₂H₅ | COOC₂H₅ | |
| 6.36 | 3-CF₃ | | C₃H₇ | | | COOCH₃ | COC₂H₅ | |
| 6.37 | 3-CF₃ | | C₃H₇ | | | COOCH₃ | COOCH₂CH=CH₂ | |
| 6.38 | 4-OCH₃ | | CH₃ | | | COOCH₃ | COOCH₂C≡CH | |
| 6.39 | 3-OCH₃ | | CH₃ | | | COOCH₃ | COOCH₃ | |
| 6.40 | 3-OC₂H₅ | 170 | CH₃ | | | COOCH₃ | COOCH₃ | |
| 6.41 | 3-CN | | CH₃ | | | COOCH₃ | COOCH₃ | |
| 6.42 | 3-CN | | C₂H₅ | | | COOCH₃ | COOCH₃ | |
| 6.43 | 3-CN | | C₃H₇ | | | COOCH₃ | COOCH₃ | |
| 6.44 | 3-CN | | CH₂OCH₃ | | | COOCH₃ | COOCH₃ | |

EXAMPLE 7.1

37 Grams of 2-amino-5-phenoxysulfonyl-acetanilide in 250 ml of methanol are heated for 5 hours under reflux together with 25 g of N,N'-bis-methoxycarbonyl-isothio-urea-S-methylether and 0.01 g of p-toluene-sulfonic acid. Subsequently the solvent is distilled off under reduced pressure, and the residue is stirred with ethyl acetate. The precipitated N-(2-acetamino-4-phenoxysulfonyl-phenyl)-N',N''-bis-methoxycarbonyl-guanidine is filtered off in the form of crystals and washed with ethyl acetate and methanol.

For the preparation of the 2-amino-5-phenoxysulfonyl-acetanilide, 40 g of 2-nitro-5-phenoxysulfonyl-acetanilide in 500 ml of methanol are hydrogenated with Raney nickel under normal pressure. The catalyst is filtered off, and the filtrate is concentrated under reduced pressure. The residue can be processed directly in the manner described above, without further purification.

For the preparation of the 2-nitro-5-phenoxysulfonyl-acetanilide, 50 g of 2-nitro-5-phenoxysulfonyl-aniline in 250 ml of acetanhydride are mixed, while stirring, with 1 ml of concentrated H₂SO₄, in which process the reaction mixture is heated. The stirring is continued for another 2 hours, and the mixture is then concentrated under reduced pressure. Diisopropylether is added to the solid residue, and the crystallized 2-nitro-5-phenoxysulfonyl-acetanilide which has precipitated is filtered off.

For the preparation of the 2-nitro-5-phenoxysulfonyl-aniline, 54 g of 2-nitro-5-phenoxysulfonyl-chlorobenzene in 500 ml of dioxan are kept for 5 hours in an autoclave with gaseous ammonia at 50° C. and at 5 atmospheres gage, and thereafter the solvent is distilled off under reduced pressure. 200 Milliliters of a mixture of equal parts of methanol and water are added to the residue. After a short time, the 2-nitro-5-phenoxysulfonyl-aniline precipitates in a crystalline form.

For the preparation of the 2-nitro-5-phenoxysulfonyl-chlorobenzene, 51 g of 4-nitro-3-chloro-benzene-sulfonic acid chloride in 120 ml of acetone are mixed with 18.8 g of phenol, and 28 ml of triethylamine are added dropwise under cooling, at an internal temperature not exceeding 10° C. After stirring the mixture for several hours at room temperature, water is added, in which process an oil separates which is worked up over ether. The yield of 2-nitro-5-phenoxysulfonyl-chlorobenzene is 54 g.

7.2 In an analogous manner, there are prepared from 2-amino-5-phenoxysulfonyl-acetanilide and 7.3 N,N'-bis-ethoxycarbonyl-isothio-urea-S-methylether, the N-(2-acetamido-4-phenoxysulfonyl-phenyl)-N',N''-bis-ethoxycarbonyl-guanidine 7.4 N,N'-bis-propoxycarbonyl-isothio-urea-S-methylether, the N-(2-acetamido-4-phenoxysulfonyl-phenyl)-N',N''-bis-propoxycarbonyl-guanidine 7.5 N,N'-bis-isopropoxycarbonyl-isothio-urea-S-methylether, the N-(2-acetamido-4-phenoxysulfonyl-phenyl)-N',N''-bis-isopropoxycarbonyl-guanidine 7.6 N,N'-bis-butoxycarbonyl-isothio-urea-S-methylether, the N-(2-acetamido-4-phenoxysulfonyl-phenyl)-N',N''-bis-butoxycarbonyl-guanidine 7.7 N,N'-bis-isobutoxycarbonyl-isothio-urea-S-methylether, the N-(2-acetamido-4-phenoxysulfonyl-phenyl)-N',N''-bis-isobutoxycarbonyl-guanidine 7.8 N-methoxycarbonyl-N'-propionyl-isothio-urea-S-methylether, the N-(2-acetamido-4-phenoxysulfonyl-phenyl)-N'-methoxycarbonyl-N''-propionyl-guanidine 7.9 N-ethoxycarbonyl-N'-benzoyl-isothio-urea-S-methylether, the N-(2-acetamido-4-phenoxysulfonyl-phenyl)-N'-ethoxycarbonyl-N''-benzoyl-guanidine 7.10 N-methoxycarbonyl-N'-cyclohexylcarbonyl-isothio-urea-S-methylether, the N-(2-acetamido-4-phenoxysulfonyl-phenyl)-N'-methoxycarbonyl-N''-cyclohexylcarbonyl-guanidine 7.11 N-methoxycarbonyl-N'-ethoxymethylcarbonyl-isothio-urea-S-methylether, the N-(2-acetamido-4-phenoxysulfonyl-phenyl)-N'-methoxycarbonyl-N''-ethoxymethylcarbonyl-guanidine

EXAMPLE 8.1

According to Example 7, 27 g of 2-amino-5-phenoxysulfonyl-butyranilide are reacted with 20 g of N,N'-bis-methoxycarbonyl-isothio-urea-S-methylether, and 9 g of N-(2-butyramido-4-phenoxysulfonyl-phenyl)-N',N''-bis-methoxycarbonyl-guanidine are obtained.

For the preparation of the 2-amino-5-phenoxysulfonyl-butyranilide, 14 ml of butyrylchloride are added dropwise, while stirring at 100° C., to 29.6 g of 2-nitro-5-phenoxysulfonyl-aniline in 300 ml of toluene, and the mixture is kept under reflux for 2 hours. Thereafter the solution is concentrated under reduced pressure, and the residue is mixed with diisopropylether. The precipitated 2-nitro-5-phenoxysulfonyl-butyranilide is filtered off, washed with diisopropylether and hydrogenated according to Example 7, to give 2-amino-5-phenoxysulfonyl-butyranilide.

In an analogous manner, the following products are prepared from R-COCl, while using starting compounds that have been accordingly modified.

While using starting compounds accordingly modified, the following products are obtained in a manner analogous to that of Example 7 from

| Ex. | Step 1 | Step 2 | Product of the invention |
|---|---|---|---|
|  | R—⟨C₆H₃(NO₂)⟩—NH—CO—R with OSO₂—C₆H₅ | R—⟨C₆H₃(NH₂)⟩—NH—CO—R with OSO₂—C₆H₅ | R—⟨C₆H₃(NH—C(=N—COOCH₃)—NH—COOCH₃)⟩—NH—CO—R with OSO₂—C₆H₅ |
|  | R |  |  |
| 8.2 | —CH₂OCH₃ |  |  |
| 8.3 | —C₂H₅ |  |  |
| 8.4 | —i-C₃H₇ |  |  |
| 8.5 | —C₄H₉ |  |  |
| 8.6 | —i-C₄H₉ |  |  |
| 8.7 | —C₅H₁₁ |  |  |
| 8.8 | —i-C₅H₁₁ |  |  |
| 8.9 | —CH₂—C₆H₅ |  |  |
| 8.10 | —CH₂—O—C₆H₅ |  |  |
| 8.11 | —CO—C₆H₅ |  |  |
| 8.12 | (cyclopentyl) |  |  |
| 8.13 | (cyclohexyl) |  |  |

| Ex. | Step 1 R—⟨Cl/NO₂⟩—OSO₂—C₆H₅ | | Step 2 R—⟨NH₂/NO₂⟩—OSO₂—C₆H₅ | | Step 3 R—⟨NH—CO—R¹/NO₂⟩—OSO₂—C₆H₅ | | Step 4 R—⟨NH—CO—R¹/NH₂⟩—OSO₂—C₆H₅ | | Product of the invention R—⟨NH—CO—R¹/NH—C(=N—R²)—NH—R³⟩—OSO₂—C₆H₅ | | |
|---|---|---|---|---|---|---|---|---|---|---|---|
|  | R | M.P. °C. | | M.P. °C. | R¹ | M.P. °C. | | M.P. °C. | R¹ | R² | R³ |
| 9.1 | 4-Cl |  |  |  | CH₃ |  |  |  | CH₃ | COOCH₃ | COOCH₃ |
| 9.2 | 3-Cl |  |  |  | CH₃ |  |  |  | CH₃ | COOC₂H₅ | COOC₂H₅ |
| 9.3 | 3-Cl |  |  |  | CH₃ |  |  |  | CH₃ | COOC₃H₇ | COOC₃H₇ |
| 9.4 | 3-Cl |  |  |  | CH₃ |  |  |  | CH₃ | COOC₂H₅ | COOCH₃ |
| 9.5 | 3-Cl |  |  |  | CH₃ |  |  |  | CH₃ | COOCH₃ | COOC₂H₅ |
| 9.6 | 3-Cl |  |  |  | CH₃ |  |  |  | CH₃ | COOC₆H₅ | COOC₆H₁₁ |
| 9.7 | 3-Cl |  |  |  | CH₃ |  |  |  | CH₃ | COOCH₃ | COC₂H₅ |
| 9.8 | 3-Cl |  |  |  | CH₃ |  |  |  | CH₃ | COOCH₂CH=CH₂ | COCH₂OC₂H |
| 9.9 | 3-Cl |  |  |  | CH₃ |  |  |  | CH₃ | COOCH₃ | COOCH₃ |
| 9.10 | 3-Cl |  |  |  | C₃H₇ |  |  |  | C₃H₇ | COOCH₃ | COOCH₃ |
| 9.11 | 3-Cl |  |  |  | CH₂OCH₃ |  |  |  | CH₂OCH₃ | COOCH₃ | COOCH₃ |
| 9.12 | 2-Cl |  |  |  | C₃H₇ |  |  |  | C₃H₇ | COOCH₃ | COOCH₃ |
| 9.13 | 2,5-Cl |  |  |  | CH₃ |  |  |  | CH₃ | COOCH₃ | COOCH₃ |
| 9.14 | 3,5-Cl |  |  |  | C₃H₇ |  |  |  | C₃H₇ | COOCH₃ | COOCH₃ |
| 9.15 | 4-Br |  |  |  | CH₃ |  |  |  | CH₃ | COOCH₃ | COOCH₃ |

-continued

| Ex. | R | M.P. °C | R¹ | M.P. °C | R² | M.P. °C | R³ |
|---|---|---|---|---|---|---|---|
| 9.16 | 3-Br | | $C_2H_5$ | | $COOCH_3$ | | $COOCH_3$ |
| 9.17 | 3-Br | | $C_3H_7$ | | $COOCH_3$ | | $COOCH_3$ |
| 9.18 | 3-Br | | $CH_2OCH_3$ | | $COOCH_3$ | | $COOCH_3$ |
| 9.19 | 2-Br | | $CH_3$ | | $COOCH_3$ | | $COOCH_3$ |
| 9.20 | 4-$CH_3$ | | $CH_3$ | | $COOCH_3$ | | $COOCH_3$ |
| 9.21 | 3-$CH_3$ | | $CH_3$ | | $COOCH_3$ | | $COOCH_3$ |
| 9.22 | 3-$CH_3$ | | $C_2H_5$ | | $COOCH_3$ | | $COOCH_3$ |
| 9.23 | 3-$CH_3$ | | $C_3H_7$ | | $COOCH_3$ | | $COOCH_3$ |
| 9.24 | 3-$CH_3$ | | $CH_2OCH_3$ | | $COOCH_3$ | | $COOCH_3$ |
| 9.25 | 2-$CH_3$ | | $CH_3$ | | $COOCH_3$ | | $COOCH_3$ |
| 9.26 | 4-t.Bu | | $CH_3$ | | $COOCH_3$ | | $COOCH_3$ |
| 9.27 | 2,4-$CH_3$ | | $CH_3$ | | $COOCH_3$ | | $COOCH_3$ |
| 9.28 | 2-Cl-4-$CH_3$ | | $CH_3$ | | $COOCH_3$ | | $COOCH_3$ |
| 9.29 | 3,5-Cl | | $CH_3$ | | $COOCH_3$ | | $COOCH_3$ |
| 9.30 | 3-$CF_3$ | | $CH_2OCH_3$ | | $COOCH_3$ | | $COOCH_3$ |
| 9.31 | 3-$CF_3$ | $C_2H_5$ | $COOCH_3$ | $COOCH_3$ | $COOCH_3$ | | $COOCH_3$ |
| 9.32 | 3-$CF_3$ | | $C_3H_7$ | | $COOC_2H_5$ | | $COOC_2H_5$ |
| 9.33 | 3-$CF_3$ | | $C_3H_7$ | | | | |
| 9.34 | 3-$CF_3$ | $C_3H_7$ | $COOCH_3$ | $COOCH_3$ | $COOCH_3$ | | $COOCH_3$ |
| 9.35 | 3-$CF_3$ | | $COC_2H_5$ | | $COOCH_3$ | | $COOCH_2CH=CH_2$ |
| 9.36 | 3-$CF_3$ | | $C_3H_7$ | | $COOCH_3$ | | $COOCH_2C≡CH$ |
| 9.37 | 4-$OCH_3$ | | $C_3H_7$ | | $COOCH_3$ | | $COOCH_3$ |
| 9.38 | 3-$OCH_3$ | | $CH_3$ | | $COOCH_3$ | | $COOCH_3$ |
| 9.39 | 3-$OC_2H_5$ | | $CH_3$ | | $COOCH_3$ | | $COOCH_3$ |
| 9.40 | 3-CN | $CH_3$ | $COOCH_3$ | $COOCH_3$ | | | |
| 9.41 | 3-CN | $C_2H_5$ | $COOCH_3$ | $COOCH_3$ | | | |
| 9.42 | 3-CN | $C_3H_7$ | $COOCH_3$ | $COOCH_3$ | | | |
| | | $CH_2OCH_3$ | $COOCH_3$ | | | | |

EXAMPLE 10.1

34 Grams of 2-amino-5-phenylsulfonyloxy-acetanilide in 200 ml of methanol are heated under reflux for 5 hours with 40 g of N,N'-bis-methoxycarbonyl-isothio-urea-S-methylether and 0.01 g of p-toluene-sulfonic acid. Subsequently the solvent is distilled off under reduced pressure, and the residue is stirred with ethyl acetate. The N-(2-acetamido-4-phenylsulfonyloxy-phenyl)-N',N"-bis-methoxycarbonyl-guanidine having precipitated in a crystalline form is filtered off and washed with ethyl acetate and methanol.

For the preparation of the 2-amino-5-phenylsulfonyloxy-acetanilide, 50 g of 2-nitro-5-phenylsulfonyloxy-acetanilide in 250 ml of methanol are hydrogenated in the presence of Raney nickel under normal pressure at room temperature. The solution is filtered off from the catalyst, the latter is washed with dimethylformamide, and the filtrate is concentrated under reduced pressure. The remaining 2-amino-4-phenylsulfonyloxy-acetanilide is pure enough for further processing.

For the preparation of the 2-nitro-5-phenylsulfonyloxy-acetanilide, 1 ml of concentrated $H_2SO_4$ is added, while stirring, to 48 g of 2-nitro-5-phenylsulfonyloxy-aniline in 250 ml of acetanhydride, in which process the reaction mixture is heated. The stirring is continued for another 2 hours, and the mixture is then concentrated under reduced pressure. The oily residue is worked up over ethyl acetate, and a solid residue of 2-nitro-5-phenylsulfonyloxy-acetanilide is obtained. It is dissolved in 100 ml of hot methanol for purification and is diluted with 100 ml of water. After cooling, the 2-nitro-4-phenylsulfonyloxy-acetanilide is filtered off and washed with water.

For the preparation of the 2-nitro-5-phenylsulfonyloxy-aniline, 15.4 g of 4-nitro-3-amino-phenol in 100 ml of acetone are mixed with 14 ml of triethylamine, and a solution of 17.6 g of benzene-sulfonic acid chloride in 30 ml of acetone is added dropwise, while stirring, at a temperature not excedding 20° C., in an ice bath. After stirring for 3 hours, the triethylamine-hydrochloride is filtered off, and the filtrate is evaporated to dryness. It is then stirred with 50 ml of methanol, and the precipitated 2-nitro-5-phenylsulfonyloxy-aniline is filtered off and washed with methanol.

In an analogous manner, there are prepared from 2-amino-5-phenyl-sulfonyloxy-acetanilide and 10.2  N,N'-bis-ethoxycarbonyl-isothio-urea-S-methylether, the N-(2-acetamido-4-phenylsulfonyloxy-phenyl)-N',N"-bis-ethoxycarbonyl-guanidine 10.3  N,N'-bis-propoxycarbonyl-isothio-urea-S-methylether, the N-(2-acetamido-4-phenylsulfonyloxy-phenyl)-N',N"-bis-propoxycarbonyl-guanidine 10.4  N,N'-bis-isopropoxycarbonyl-isothio-urea-S-methylether, the N-(2-acetamido-4-phenylsulfonyloxy-phenyl)-N',N"-bis-isopropoxycarbonyl-guanidine 10.5  N,N'-bis-butoxycarbonyl-isothio-urea-S-methylether, the N-(2-acetamido-4-phenylsulfonyloxy-phenyl)-N',N"-bis-butoxycarbonyl-guanidine 10.6  N,N'-bis-isobutoxycarbonyl-isothio-urea-S-methylether, the N-(2-acetamido-4-phenylsulfonyloxy-phenyl)-N',N"-bis-isobutoxycarbonyl-guanidine 10.7  N-methoxycarbonyl-N'-propionyl-isothio-urea-S-methylether, the N-(2-acetamido-4-phenylsulfonyloxy-phenyl)-N'-methoxycarbonyl-N"-propionyl-guanidine 10.8  N-ethoxycarbonyl-N'-benzoyl-isothio-urea-S-methylether, the N-(2-acetamido-4-phenylsulfonyloxy-phenyl)-N'-ethoxycarbonyl-N"-benzoyl-guanidine 10.9  N-methoxycarbonyl-N'-cyclohexylcarbonyl-isothio-urea-S-methylether, the N-(2-acetamido-4-phenylsulfonyl-phenyl)-N'-methoxycarbonyl-N"-cyclohexylcarbonyl-guanidine 10.10  N-methoxycarbonyl-N'-ethoxymethylcarbonyl-isothio-urea-S-methylether, the N-(2-acetamido-4-phenylsulfonyloxy-phenyl)-N'-methoxycarbonyl-N"-ethoxymethylcarbonyl-guanidine

EXAMPLE 11.1

In a manner analogous to that of Example 10, 27 g of 2-amino-5-phenylsulfonyloxy-butyranilide are reacted with 20 g of N,N'-bis-methoxycarbonyl-isothio-urea-S-methylether, and 9 g of N-(2-butyramido-4-phenylsulfonyloxy-phenyl)-N',N"-bis-methoxycarbonyl-guanidine are obtained.

For the preparation of the 2-amino-5-phenylsulfonyloxy-butyranilide, 14 ml of butyrylchloride are added dropwise, while stirring at 100° C., to 29.6 g of 2-nitro-5-phenoxysulfonyl-aniline in 300 ml of toluene, and the mixture is kept under reflux for 2 hours. Thereafter the solution is concentrated under reduced pressure, and the residue is mixed with diisopropylether. The precipitated 2-nitro-4-phenylsulfonyloxy-butyranilide is filtered off, washed with diisopropylether and hydrogenated according to Example 10, to give 2-amino-5-phenylsulfonyloxy-butyranilide.

In an analogous manner, the following products are prepared, while using starting compounds that have been accordingly modified.

| Step 1 | Step 2 | Product of the invention |
|---|---|---|

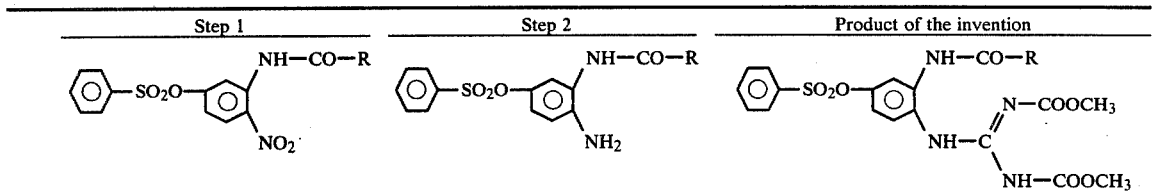

| Ex. | R |
|---|---|
| 11.2 | —CH$_2$—OCH$_3$ |
| 11.3 | —C$_2$H$_5$ |
| 11.4 | -i-C$_3$H$_7$ |
| 11.5 | —C$_4$H$_9$ |
| 11.6 | -i-C$_4$H$_9$ |

-continued

| | Step 1 | Step 2 | Product of the invention |
|---|---|---|---|

(structures shown across columns with R group variations)

| Ex. | R |
|---|---|
| 11.7 | —C$_5$H$_{11}$ |
| 11.8 | -i-C$_5$H$_{11}$ |
| 11.9 | —CH$_2$—C$_6$H$_5$ |
| 11.10 | —CH$_2$—O—C$_6$H$_5$ |
| 11.11 | —CO—C$_6$H$_5$ |
| 11.12 | cyclopentyl |
| 11.13 | cyclohexyl |

While using starting compounds accordingly modified, the following products are obtained in a manner analogous to that of Example 10 from While using starting compounds accordingly modified, the following products are obtained in a manner analogous to that of Example 10 from

| | Step 1 | | Step 2 | | Step 3 | | Products of the invention | | |
|---|---|---|---|---|---|---|---|---|---|
| Ex. | R | M.P. °C. | $R^1$ | M.P. °C. | | M.P. °C. | $R^1$ | $R^2$ | $R^3$ |
| 12.1 | 4-Cl | | $CH_3$ | | | | | $COOCH_3$ | $COOCH_3$ |
| 12.2 | 3-Cl | | $CH_3$ | | | | | $COOCH_3$ | $COOCH_3$ |
| 12.3 | 3-Cl | | $CH_3$ | | | | | $COOC_2H_5$ | $COOC_2H_5$ |
| 12.4 | 3-Cl | | $CH_3$ | | | | | $COOC_3H_7$ | $COOC_3H_7$ |
| 12.5 | 3-Cl | | $CH_3$ | | | | | $COOCH_3$ | $COOC_2H_5$ |
| 12.6 | 3-Cl | | $CH_3$ | | | | | $COOCH_3$ | $COOC_6H_{11}$ |
| 12.7 | 3-Cl | | $CH_3$ | | | | | $COOCH_3$ | $COOC_2H_5$ |
| 12.8 | 3-Cl | | $CH_3$ | | | | | $COOCH_3$ | $COOCH_2OC_2H_5$ |
| 12.9 | 3-Cl | | $CH_3$ | | | | | $COOCH_2CH=CH_2$ | $COOCH_3$ |
| 12.10 | 3-Cl | | $C_3H_7$ | | | | | $COOCH_3$ | $COOCH_3$ |
| 12.11 | 3-Cl | | $CH_2OCH_3$ | | | | | $COOCH_3$ | $COOCH_3$ |
| 12.12 | 2-Cl | | $C_3H_7$ | | | | | $COOCH_3$ | $COOCH_3$ |
| 12.13 | 2,5-Cl | | $CH_3$ | | | | | $COOCH_3$ | $COOCH_3$ |
| 12.14 | 3,5-Cl | | $C_3H_7$ | | | | | $COOCH_3$ | $COOCH_3$ |
| 12.15 | 4-Br | | $CH_3$ | | | | | $COOCH_3$ | $COOCH_3$ |
| 12.16 | 3-Br | | $C_2H_5$ | | | | | $COOCH_3$ | $COOCH_3$ |
| 12.17 | 3-Br | | $C_3H_7$ | | | | | $COOCH_3$ | $COOCH_3$ |
| 12.18 | 3-Br | | $CH_2OCH_3$ | | | | | $COOCH_3$ | $COOCH_3$ |
| 12.19 | 2-Br | | $CH_3$ | | | | | $COOCH_3$ | $COOCH_3$ |
| 12.20 | 4-$CH_3$ | | $CH_3$ | | | | | $COOCH_3$ | $COOCH_3$ |
| 12.21 | 3-$CH_3$ | | $CH_3$ | | | | | $COOCH_3$ | $COOCH_3$ |
| 12.22 | 3-$CH_3$ | | $C_2H_5$ | | | | | $COOCH_3$ | $COOCH_3$ |
| 12.23 | 3-$CH_3$ | | $C_3H_7$ | | | | | $COOCH_3$ | $COOCH_3$ |
| 12.24 | 3-$CH_3$ | | $CH_2OCH_3$ | | | | | $COOCH_3$ | $COOCH_3$ |
| 12.25 | 2-$CH_3$ | | $CH_3$ | | | | | $COOCH_3$ | $COOCH_3$ |
| 12.26 | 4-t.Bu | | $CH_3$ | | | | | $COOCH_3$ | $COOCH_3$ |
| 12.27 | 2,4-$Cl$-$CH_3$ | | $CH_3$ | | | | | $COOCH_3$ | $COOCH_3$ |
| 12.28 | 2-Cl-4-$CH_3$ | | $CH_3$ | | | | | $COOCH_3$ | $COOCH_3$ |
| 12.29 | 3,5-Cl | | $CH_3$ | | | | | $COOCH_3$ | $COOCH_3$ |
| 12.30 | 3-$CF_3$ | | $CH_3$ | | | | | $COOCH_3$ | $COOCH_3$ |
| 12.31 | 3-$CF_3$ | | $C_2H_5$ | | | | | $COOCH_3$ | $COOCH_3$ |
| 12.32 | 3-$CF_3$ | | $C_3H_7$ | | | | | $COOCH_3$ | $COOCH_3$ |
| 12.33 | 3-$CF_3$ | | $CH_3$ | | | | | $COOC_2H_5$ | $COOC_2H_5$ |
| 12.34 | 3-$CF_3$ | | $CH_3$ | | | | | $COOCH_3$ | $COOC_2H_5$ |
| 12.35 | 3-$CF_3$ | | $C_3H_7$ | | | | | $COOCH_3$ | $COOCH_2CH=CH_2$ |
| 12.36 | 3-$CF_3$ | | $C_3H_7$ | | | | | $COOCH_3$ | $COOCH_2C\equiv CH$ |
| 12.37 | 4-$OCH_3$ | | $CH_3$ | | | | | $COOCH_3$ | $COOCH_3$ |
| 12.38 | 3-$OCH_3$ | | $CH_3$ | | | | | $COOCH_3$ | $COOCH_3$ |
| 12.39 | 3-$OC_2H_5$ | | $CH_3$ | | | | | $COOCH_3$ | $COOCH_3$ |
| 12.40 | 3-CN | | $CH_3$ | | | | | $COOCH_3$ | $COOCH_3$ |
| 12.41 | 3-CN | | $C_2H_5$ | | | | | $COOCH_3$ | $COOCH_3$ |
| 12.42 | 3-CN | | $C_3H_7$ | | | | | $COOCH_3$ | $COOCH_3$ |
| 12.43 | 3-CN | | $CH_2OCH_3$ | | | | | $COOCH_3$ | $COOCH_3$ |

We claim:

1. A substituted phenylguanidine of the general formula:

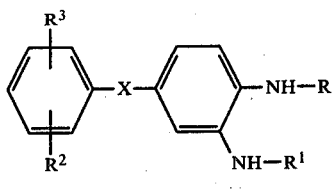

in which
R and R₁ are different and each represent one of the radicals

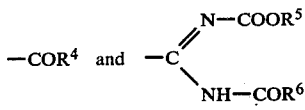

R⁴ is a radical selected from alkyl of 1 to 6 carbons, cycloalkyl of 3 to 10 carbons, carbocyclic aryl of 6 to 10 carbons, amino, alkoxy of 1 to 4 carbons, carbocyclic aralkyl with 6 to 10 carbons in the aryl moiety, and the alkyl radical may be substituted by methoxy, R⁵ is alkyl of 1 to 6 carbons, R⁶ is hydrogen or a radical selected from alkyl of 1 to 6 carbons, cycloalkyl of 3 to 10 carbons, alkoxy of 1 to 4 carbons, carbocyclic aryl of 6 to 10 carbons, and carbocyclic aralkyl with 6 to 10 carbons in the aryl moiety, R² and R³ may be different and are selected from hydrogen, alkoxy of 1 to 4 carbons, halogen, trifluoromethyl, alkyl of 1 to 4 carbons and CN, and X is the group —O—SO₂— or —SO₂O—.

2. A compound of the formula:

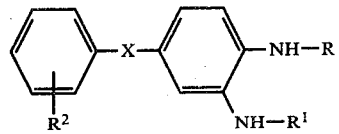

in which
R² is hydrogen, halo, cyano, trifluoromethyl, alkoxy of 1–4 carbon atoms or alkyl of 1–4 carbon atoms;
R and R¹ are different and each represent one of the radicals

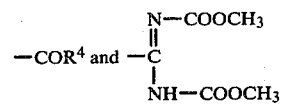

wherein R⁴ is alkyl of 1–6 carbon atoms; and
X is —O—SO₂— or —SO₂O—.

3. N-(2-methoxyacetamido-5-phenylsulfonyloxyphenyl)-N',N''-bis-methoxycarbonyl-guanidine.

4. N-(2-propionamido-5-phenylsulfonyloxy-phenyl)-N',N''-bis-methoxycarbonyl-guanidine.

5. N-[2-acetamido-5-(3-trifluoromethyl-phenylsulfonyloxy-phenyl)]-N',N''-methoxycarbonyl-guanidine.

6. A pharmaceutical composition for treating helmintic infections in mammals containing as the active ingredient an effective amount of a substituted phenylguanidine as claimed in claim 1, in admixture with a pharmaceutically suitable carrier.

7. A method of treating helminthic infections in mammals by administering to a patient an effective amount of a compound as claimed in claim 1.

8. A pharmaceutical composition for treating helminthic infections in mammals containing as the active ingredient an anthelmintically effective amount of a compound as claimed in claim 2 in admixture with a pharmaceutically suitable carrier.

9. A method for treating helminthic infections in mammals which comprises administering to said mammals an anthelmintically effective amount of a compound of claim 2.

* * * * *